US005795579A

United States Patent [19]
Burke et al.

[11] Patent Number: 5,795,579
[45] Date of Patent: Aug. 18, 1998

[54] HERPES SIMPLEX VIRUS VP16 VACCINES

[75] Inventors: Rae Lyn Burke, San Francisco; Rose E. Sekulovich, Berkeley, both of Calif.

[73] Assignee: Chiron Corporation, Emeryville, Calif.

[21] Appl. No.: 442,980

[22] Filed: May 17, 1995

Related U.S. Application Data

[62] Division of Ser. No. 322,729, Oct. 13, 1994, Pat. No. 5,714,152, which is a continuation of Ser. No. 133,974, Oct. 8, 1993, abandoned, which is a continuation of Ser. No. 561,528, Aug. 2, 1990, abandoned.

[51] Int. Cl.$^6$ .................. A61K 39/245; C07K 1/00; C07K 14/00; C07K 17/00
[52] U.S. Cl. .................. 424/231.1; 530/350; 530/395
[58] Field of Search .................. 424/231.1; 530/350, 530/395

[56] References Cited

U.S. PATENT DOCUMENTS

| | | |
|---|---|---|
| 4,618,578 | 10/1986 | Burke et al. |
| 4,642,333 | 2/1987 | Person |
| 4,661,349 | 4/1987 | Kino et al. |
| 4,818,694 | 4/1989 | Watson et al. |
| 4,855,224 | 8/1989 | Berman et al. |
| 4,859,587 | 8/1989 | Roizman |
| 4,891,315 | 1/1990 | Watson et al. |
| 5,171,568 | 12/1992 | Burke et al. ............ 424/89 |

FOREIGN PATENT DOCUMENTS

| | | |
|---|---|---|
| 0 133 063 | 2/1985 | European Pat. Off. |
| WO 85/04587 | 10/1985 | WIPO |
| WO 88/02634 | 4/1988 | WIPO |

OTHER PUBLICATIONS

Berman et al., *Science* (1983) 222:524–527.
Berman et al., *Science* (1985) 227:1490–1492.
Bzik et al., *Virology* (1984) 133:301–314.
Campbell et al., *J. Mol. Biol.* (1984) 180:1–19.
Capone et al., *Mol. Cell. Biochem.* (1990) 94(1):45–52.
Cohen et al., *J. Virol.* (1984) 49(1):102–108.
Cress et al., *Gene* (1991) 103:235–238.
Eberle et al., *J. Gen. Virol.* (1984) 65:1839–1843.
Koelle et al., *J. of Virol.* (1994) 68(5):2803–2810.
Lasky et al., *Bio/Technology* (Jun. 1984) pp. 527–532.
McLean et al., *J. Gen. Virol.* (1982) 639:297–305.
Moss et al., *J. Gen. Virol.* (1982) 70:1579–1585.
Pachl et al., *J. Virol.* (1987) 61(2):315–325.
Pellett et al., *Proc. Natl. Acad. Sci.* (1985) 82:5870–5874.
Sadowski et al., *Nature* (1988) 335:563–564.
Stanberry et al., *J. Infect. Dis.* 155(5):914–920.
Stringer et al., *Nature* (1990) 345:783–786.
Stuve et al., *J. Virol.* (1987) 61(2):326–335.
Triezenberg et al., *Genes and Development* 2:718–729.
Watson et al., *Science* (1982) 218:381–384.
Weiss et al., *Nature* (1983) 302:72–74.
Meignier, et al, 1987, "Immunization of Experimental Animals . . . " J. I. D. 155(5):921–930.

*Primary Examiner*—Lynette F. Smith
*Attorney, Agent, or Firm*—Roberta L. Robins; Barbara G. McClung; Robert P. Blackburn

[57] ABSTRACT

Compositions which are useful for treatment of individuals for Herpes Simplex Virus (HSV) infections are provided, as are methods for their use. These compositions are comprised of immunogenic polypeptides which are comprised of an epitope of HSV VP16; they may also be comprised of an epitope of an HSV glycoprotein. Also provided are polypeptides which are used in the compositions for treating individuals for HSV infection, and methods and compositions used in the production of the polypeptides.

16 Claims, 22 Drawing Sheets

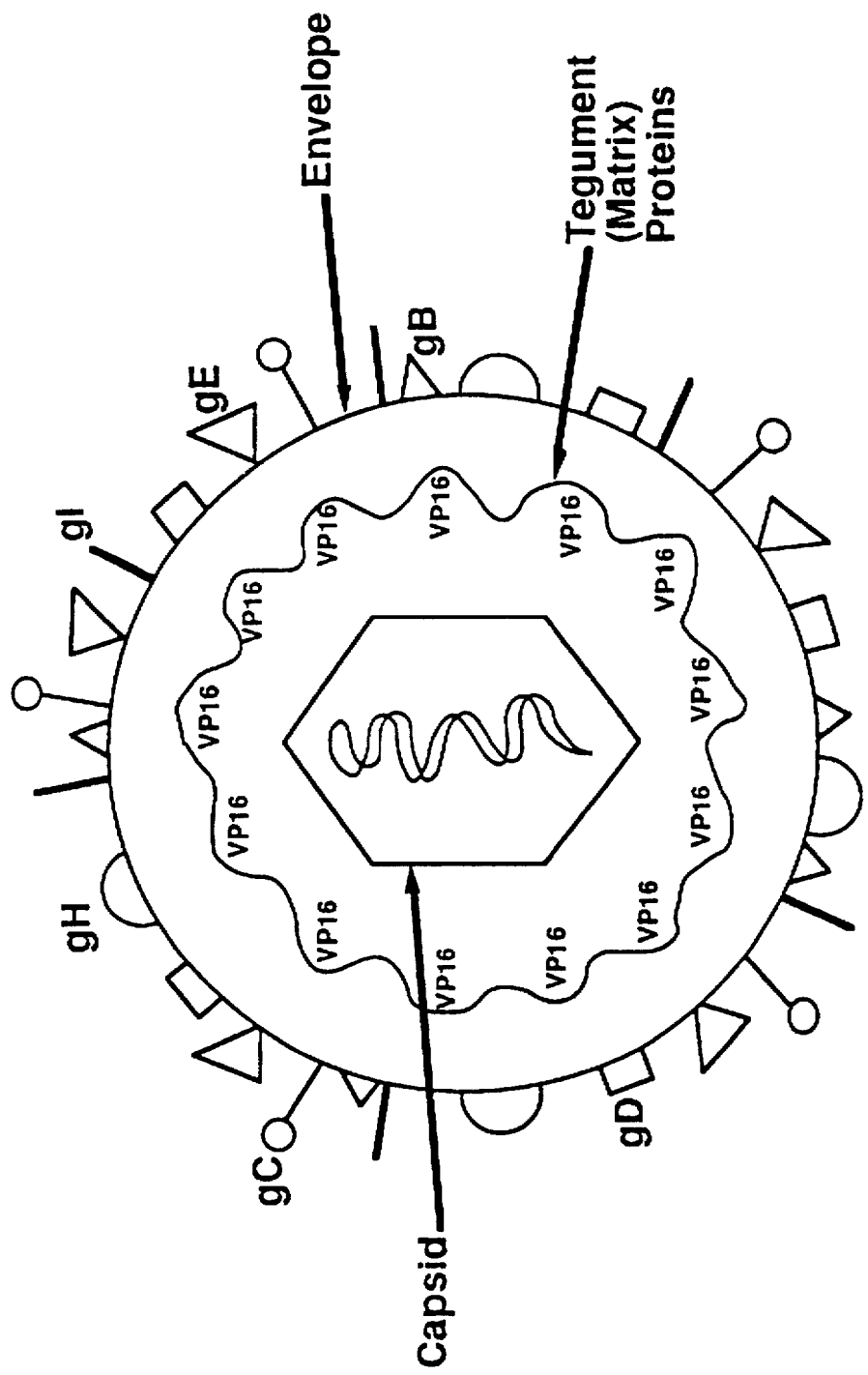
HSV-2 Virion   FIG. 1

```
0    [MDLLVD] e [LFAD] mn [ADG] a [SPPPPRPAGGPKNTPAAPPLYATGRLSQAQLMPSPPMPV
0    [MDLLVD] d [LFAD] .. [ADG] v [SPPPPRPAGGPKNTPAAPPLYATGRLSQAQLMPSPPMPV

56   PPAALFNRLLDDLGFSAGPALCTMLDTWNEDLFS] al [PTNAD] l [YRECKFLSTLPSDV] ve [
54   PPAALFNRLLDDLGFSAGPALCTMLDTWNEDLFS] gf [PTNAD] m [YRECKFLSTLPSDV] id [

114  WGDA] y [VPER] tq [IDIRAHGDVAFPTLPATRD] glgl [YYEA] lsr [FF] ha [ELRAR
112  WGDA] h [VPER] sp [IDIRAHGDVAFPTLPATRD] elps [YYEA] maq [FF] rg [ELRAR 164  EESYRTVLANFCSALYRYLRASVRQLHRQAHMRGR] d [RDL] g [EMLR] a [TIADRYYRETARL
162  EESYRTVLANFCSALYRYLRASVRQLHRQAHMRGR] n [RDL] r [EMLR] t [TIADRYYRETARL 222  ARVLFLHLYLFL] t [REILWAAYAEQMMRPDLFD] c [LCCDLESWRQLA] g [LFQP] f [MF]
220  ARVLFLHLYLFL] s [REILWAAYAEQMMRPDLFD] g [LCCDLESWRQLA] c [LFQP] l [MF]

275  v [NG] a [LTVRGVP] i [EARRLRELNHIREHLNLPLVRSAA] t [EEPGAPLTTPP] tlh [
273  i [NG] s [LTVRGVP] v [EARRLRELNHIREHLNLPLVRSAA] a [EEPGAPLTTPP] vlq [

326  GNQAR] a [SGYFM] v [LIRAKLDSYSS] ft [TS] psea [VMREHAYSR] a [RT] k [NN
324  GNQAR] s [SGYFM] l [LIRAKLDSYSS] va [TS] eges [VMREHAYSR] g [RT] r [NN 372  YGSTIEGLLDLP] . [DDDAP] e [EAGL] a [APR] l [SFL] p [AG] ht. [RRLS] . [
370  YGSTIEGLLDLP] d [DDDAP] a [EAGL] v [APR] m [SFL] s [AG] qrp [RRLS] t [

411  TAP] p [TDVSLGDEL] h [LDGE] dvamah [ADALDDFDL] d [MLGD] gd [SP] g [PG]
412  TAP] i [TDVSLGDEL] r [LDGE] evdmtp [ADALDDFDL] e [MLGD] ve [SP] s [PG]

456  ftp [HD] sap [YGALD] ma [DFEFEQMFTDALGID] ey [GG]
457  mt. [HD] pvs [YGALD] vd [DFEFEQMFTDALGID] df [GG]
```

FIG. 2

Translation of vp16final frame 1

| | | | | | | | | | |
|---|---|---|---|---|---|---|---|---|---|
| Arg | Ser | Leu | Phe | Pro | Asp | Pro | Thr | Ala | Pro |
| AGA | TCG | TTA | TTC | CCG | GAC | CCA | ACC | GCC | CCC |

Met Asp Leu Leu Val Asp Asp Leu Phe Ala
ATG GAC CTG TTG GTC GAC GAT CTG TTT GCG

Asp Ala Asp Gly Val Ser Pro Pro Pro Arg
GAC GCG GAC GGG GTT TCG CCA CCG CCC AGG

Pro Ala Gly Gly Pro Lys Asn Thr Pro
CCA GCC GGG GGT CCC AAG AAC ACC CCA

Ala Ala Pro Pro Leu Tyr Ala Thr Gly Arg
GCC GCC CCT CCG TAC GCC ACC GGT CGG

Leu Ser Gln Ala Gln Leu Met Pro Ser Pro
CTG AGT CAG GCC CAG CTG ATG CCC TCG CCG

Pro Met Pro Val Pro Pro Ala Ala Leu Phe
CCC ATG CCC GTC CCC CCC GCG GCC CTG

Asn Arg Leu Leu Asp Asp Leu Gly Phe Ser
AAC CGT CTC GAC GAT CTG GGC TTC AGC

Ala Gly Pro Ala Leu Cys Thr Met Leu Asp
GCG GGT CCC GCG CTG TGT ACC ATG CTG GAT

Leu Phe Ser Gly Phe
CTA GAT ACC TGG AAC GAG GAC CTG TCT GGG TTC

Pro Thr Asn Ala Asp Met Tyr Arg Glu Cys Lys Phe Leu Ser Thr Leu Pro Ser Asp Val
CCG ACC AAC GCC GAC ATG TAC CGG GAG TGC AAG TTT CTG TCG ACG CTG CCC AGC GAC GTG

Ile Asp Trp Gly Asp Ala His Val Pro Glu Arg Ser Pro Ile Asp Ile Arg Ala His Gly
ATC GAC TGG GGG GAT GCG CAC GTC CCC GAG TCC CCG ATC GAC ATT CGC GCC CAC GGC

Asp Val Ala Phe Pro Thr Leu Pro Ala Thr Arg Asp Glu Leu Pro Ser Tyr Tyr Glu Ala
GAC GTG GCG TTC CCC ACC CTG CCC GCC ACC CGC GAC GAG CTG CCT TCG TAC TAC GAG GCC

Met Ala Gln Phe Phe Arg Gly Glu Leu Arg Ala Arg Glu Glu Ser Tyr Arg Thr Val Leu
ATG GCG CAG TTC TTC CGC GGT GAG CTG CGG GCG CGG GAG GAG AGC TAC CGG ACC GTG TTG

Ala Asn Phe Cys Ser Ala Leu Tyr Arg Tyr Leu Arg Ala Ser Val Arg Gln Leu His Arg
GCA AAT TTT TGC TCG GCC CTG TAC CGG TAC CTG CGC GCC AGC GTT CGG CAG CTA CAC CGC

FIG. 3A-1

```
Gln Ala His Met Arg Gly Arg Asn Arg Asp Leu Arg Glu Met Leu Arg Thr Thr Ile Ala
CAG GCA CAC ATG CGG GGC CGC AAC CGC GAC CTG CGG GAG ATG CTG CGC ACC ACG ATC GCG

Asp Arg Tyr Arg Glu Thr Ala Arg Leu Ala Arg Val Leu Phe Leu His Leu Tyr Leu
GAC AGG TAC CGC GAG ACC GCG CTG GCG CGC GTC CTG TTT CTG CAT CTA TAC CTC

Phe Leu Ser Arg Glu Ile Leu Trp Ala Ala Tyr Ala Glu Gln Met Met Arg Pro Asp Leu
TTT CTG AGC CGC GAG ATC CTA TGG GCC GCG TAC GAG CAG ATG ATG CGG CCC GAT CTG

Phe Asp Gly Leu Cys Cys Asp Leu Glu Ser Trp Arg Gln Leu Ala Cys Leu Phe Gln Pro
TTC GAC GGC CTC TGC TGC GAC CTG GAG AGC TGG CGC CAG TTG GCG TGT CTG TTT CAG CCC

Leu Met Phe Ile Asn Gly Ser Leu Thr Val Arg Gly Val Pro Val Glu Ala Arg Arg Leu
CTG ATG TTT ATC AAC GGA TCG CTC ACC GTG CGG GGA GTT CCC GTG GAG GCC CGG CGA CTG

Arg Glu Leu Asn His Ile Arg Glu His Leu Asn Leu Pro Leu Val Arg Ser Ala Ala Ala
CGG GAG CTA AAC CAC ATT CGC GAG CAC CTG AAC CTC CCG CTG GTG CGA GCC GCG GCG

Glu Glu Pro Gly Ala Pro Leu Thr Thr Pro Pro Val Leu Gln Gly Asn Gln Ala Arg Ser
GAG GAA CCC GGG GCG CCC CTC ACG CCC CCC GTC CTG CAG GGC AAC CAG GCC CGC TCC

Ser Gly Tyr Phe Met Leu Leu Ile Arg Ala Lys Leu Asp Ser Tyr Ser Ser Val Ala Thr
TCT GGG TAC TTT ATG CTG CTG ATC CGG GCC AAG TTG GAC TCG TAC AGC AGC GTC GCC ACC

Ser Glu Gly Glu Ser Val Met Arg Glu His Ala Tyr Ser Arg Gly Arg Thr Arg Asn Asn
TCG GAG GGC GAG TCC GTC ATG CGG GAG CAC GCG TAT AGC GGG CGG ACC AGA AAC AAT

Tyr Gly Ser Thr Ile Glu Gly Leu Leu Asp Leu Leu Pro Asp Asp Ala Pro Ala Glu
TAC GGA TCG ACA ATC GAG GGC CTG CTC GAC CCG GAC GAT GCT CCC GCG GAG
```

FIG. 3A-2

```
Ala Gly Leu Val Ala Pro Arg Met Ser Phe Leu Ser Ala Gly Gln Arg Pro Arg Arg Leu
GCC GGG CTG GTG GCG CCG CGC ATG TCG TTT CTC TCC GCG GGA CAA CGC CCC CGC AGA CTG

Ser Thr Thr Ala Pro Ile Thr Asp Val Ser Leu Gly Asp Glu Leu Arg Leu Asp Gly Glu
TCC ACC ACC GCC CCC ATT ACC GAC GTC AGC CTG GGA GAC GAA CTC CGC CTG GAC GGC GAG

Glu Val Asp Met Thr Pro Ala Asp Ala Leu Asp Asp Phe Asp Leu Glu Met Leu Gly Asp
GAG GTG GAT ATG ACG CCC GCC GAC GCC CTG GAC GAC TTC GAC TTG GAG ATG CTG GGG GAC

Val Glu Ser Pro Ser Pro Gly Met Thr His Asp Pro Val Ser Tyr Gly Ala Leu Asp Val
GTG GAG TCC CCC TCC CCG GGA ATG ACC CAC GAC CCC GTC TCG TAT GGG GCT TTG GAC GTG

Asp Asp Phe Glu Phe Glu Gln Met Phe Thr Asp Ala Leu Gly Ile Asp Asp Phe Gly Gly
GAC GAT TTT GAG TTT GAA CAG ATG TTT ACC GAT GCC CTG GGC ATT GAC GAC TTT GGG GGG

AM  Asp Val Arg Pro Gly Gly Ala Pro Pro Pro Pro Pro Pro Arg Leu Thr Ser Val Cys
TAG GAT GTG CGA CCG GGC GGC GCG CCC CCC CCA CCG CCG CCC CGC CTC ACC TCC GTC TGT

Ile Ala Ile Glu Gly Ser Gln Pro Gln Gln OC  Thr
ATC GCG ATA GAG GGT TCG CAA CCA CAG CAA TAA ACA
```

FIG. 3A-3

Translated Mol. Weight = 58742.82

Codon usage:

```
15/UUU/phe   2/UCU/ser    2/UAU/tyr    3/UGU/cys
 8/UUC/phe   9/UCC/ser   14/UAC/tyr    4/UGC/cys
 1/UUA/leu   0/UCA/ser    1/UAA/OC     0/UGA/OP
 6/UUG/leu  13/UCG/ser    1/UAG/AM     4/UGG/trp 0/CUU/leu   2/CCU/pro    1/CAU/his    1/CGU/arg
12/CUC/leu  29/CCC/pro    8/CAC/his   22/CGC/arg
 5/CUA/leu   6/CCA/pro    3/CAA/gln    3/CGA/arg
40/CUG/leu  14/CCG/pro   12/CAG/gln   16/CGG/arg 4/AUU/ile   0/ACU/thr    2/AAU/asn    2/AGU/ser
 8/AUC/ile  21/ACC/thr   10/AAC/asn    9/AGC/ser
 1/AUA/ile   2/ACA/thr    0/AAA/lys    3/AGA/arg
18/AUG/met   4/ACG/thr    3/AAG/lys    2/AGG/arg 3/GUU/val   2/GCU/ala   10/GAU/asp    5/GGU/gly
10/GUC/val  23/GCC/ala   35/GAC/asp   11/GGC/gly
 0/GUA/val   2/GCA/ala    3/GAA/glu    6/GGA/gly
11/GUG/val  25/GCG/ala   28/GAG/glu   12/GGG/gly
```

FIG. 3B-1 frame 2

| Asp | Arg | Tyr | Ser | Arg | Thr | Gln | Pro | Pro | Trp | Thr | Cys | Trp | Ser | Thr | Ile | Cys | Leu | Arg |
|---|---|---|---|---|---|---|---|---|---|---|---|---|---|---|---|---|---|---|
| GAT | CGT | TAT | TCC | CGG | ACC | CAA | CCG | CCC | TGG | ACC | TGT | TGG | TCG | ACG | ATC | TGT | TTG | CGG |

| Thr | Arg | Thr | Gly | Phe | Arg | His | Arg | Pro | Pro | Gly | Gln | Pro | Gly | Val | Pro | Arg | Thr | Pro | Gln |
|---|---|---|---|---|---|---|---|---|---|---|---|---|---|---|---|---|---|---|---|
| ACG | CGG | ACG | GGG | TTT | CGC | CAC | CGC | CCA | CCC | GGC | CAG | CCG | GGG | GTC | CCA | AGA | ACA | CCC | CAG |

| Pro | Pro | Leu | Arg | Cys | Thr | Pro | Pro | Val | Gly | OP  | Val | Arg | Pro | Ser | OP  | Cys | Pro | Arg | Arg |
|---|---|---|---|---|---|---|---|---|---|---|---|---|---|---|---|---|---|---|---|
| CCC | CCC | CTC | CGC | TGC | ACG | CCA | CCG | GTC | GGC | TGA | GTC | AGG | CCC | AGC | TGA | TGC | CCT | CGC | CGC |

| Pro | Cys | Pro | Ser | Pro | Pro | Arg | Pro | Cys | Leu | Thr | Val | Ser | Ser | Thr | Ile | Trp | Ala | Ser | Ala |
|---|---|---|---|---|---|---|---|---|---|---|---|---|---|---|---|---|---|---|---|
| CCA | TGC | CCG | TCC | CCC | CCG | AGG | CCC | TGT | TTA | ACC | GTC | TCC | TCG | ACG | ATC | TGG | GCT | TCA | GCG |

| Arg | Val | Pro | Arg | Cys | Val | Pro | Cys | AM  | Ile | Pro | Gly | Thr | Arg | Thr | Cys | Ser | Leu | Gly | Ser |
|---|---|---|---|---|---|---|---|---|---|---|---|---|---|---|---|---|---|---|---|
| CGG | GTC | CCG | CGC | TGT | GTA | CCA | TGC | TAG | ATA | CCT | GGA | ACG | AGG | ACC | TGT | TCT | CTG | GGT | TCC |

| Arg | Pro | Thr | Cys | Thr | Gly | Ser | Ala | Ser | Phe | Cys | Arg | Arg | Cys | Pro | Ala | Thr | OP  |
|---|---|---|---|---|---|---|---|---|---|---|---|---|---|---|---|---|---|

HERPES SIMPLEX VIRUS VP16 VACCINES

This application is a divisional of application Ser. No. 08/322,779, filed Oct. 13, 1994, allowed as U.S. Pat. No. 5,914,152, which is a continuation of application Ser. No. 08/133,974, filed Oct. 8, 1993, abandoned, which is a continuation of application Ser. No. 07/561,528, filed Aug. 2, 1990, abandoned.

TECHNICAL FIELD

This invention relates to materials and methodologies for the alleviation of herpes virus infections. More specifically, it relates to compositions containing a polypeptide comprised of an immunogenic epitope of VP16, including VP16 and fragments thereof, and to methods for preparing the polypeptides for the composition.

BACKGROUND

The herpes viruses include the herpes simplex viruses (HSV), comprising two closely related variants designated types 1 (HSV-1) and 2 (HSV-2). Herpes simplex virus (HSV) is a prevalent cause of genital infection in humans, with an estimated annual incidence of 600,000 new cases and with 10 to 20 million individuals experiencing symptomatic chronic recurrent disease. The asymptomatic subclinical infection rate may be even higher. Using a type-specific serological assay, researchers showed that 35% of an unselected population of women attending a health maintenance organization clinic in Atlanta had antibodies to HSV type 2 (HSV-2). Although continuous administration of antiviral drugs such as acyclovir ameliorates the severity of acute HSV disease and reduces the frequency and duration of recurrent episodes, such chemotherapeutic intervention does not abort the establishment of latency nor does it alter the status of the latent virus. As a consequence, the recurrent disease pattern is rapidly reestablished upon cessation of drug treatment. Since the main source of virus transmission arises from recrudescent disease, any approach to impact the rate of infection must ultimately require a vaccine strategy. Thus, it is a matter of great medical and scientific interest to provide safe and effective vaccines for humans to prevent HSV infection, and where infection has occurred, therapies for the disease.

HSV is a double stranded DNA virus having a genome of about 150 to 160 kbp packaged within an icosahedral capsid surrounded by a membrane envelope. The viral envelope includes at least seven virus-specific glycoproteins, including gB, gC, gD, gE, and gG, where gB and gD are cross-reactive between types 1 and 2. One approach to vaccine therapy has been the use of isolated glycoproteins, which have been shown to provide protection when injected into mice subsequently challenged with live virus.

The VP16 gene product is associated with the virion tegument, located between the capsid and the envelope (See FIG. 1). VP16, which is a virion stimulatory factor, is an abundant protein with some 500 to 1000 copies per virion. It has been alternately named ICP25, VmW65, and the α-trans-inducing factor (αTIF). The majority of studies on VP16 have explored its role in the trans-activation of the "immediate early genes" in HSV replication. In view of the internal location of VP16 in the virion, and the current state of knowledge concerning the mode of HSV replication, VP16 would not be expected to be a good candidate for use in treatment of HSV infections.

RELEVANT LITERATURE

Spear and Roizman (1972) disclose the electrophoretic separation of proteins in purified HSV1. McLean et al. (1982) discloses a monoclonal antibody which putatively interacts with VP16 from HSV1 and HSV2.

Eberle et al. (1984), discloses studies on antibody response to HSV components during primary and recurrent genital HSV-2 infections.

Campbell et al. (1984), putatively discloses a DNA sequence encoding VmW65 of HSV1, and identifies VmW65 as the major tegument virion component which trans-activates HSV immediate-early (IE) transcription.

Pellett et al. (1985) discloses the expression of cloned HSV1 α-TIF encoding sequence in transient expression systems.

Triezenberg et al. (1988), discloses a putative amino acid sequence for HSV1 VP16, and deletion mutants thereof.

McGeoch et al. (1988) presents a DNA sequence of the long unique region ($U_L$) of HSV-1 strain 17. This region includes a segment which putatively encodes, in gene UL48, the major tegument protein (which is an activator of transcription of IE genes in the newly infected cell).

REFERENCES

Barr et al. (1986), Biotechniques 4:428.

Beach and Nurse (1981), Nature 300:706.

Broach (1981) in : Molecular Biology of the Yeast Saccharomyces, Vol. 1, p.445, Cold Spring Harbor Press.

Broach et al. (1983), Meth. Enz. 101:307.

Campbell et al. (1984), J. Mol. Biol. 180:1.

Chakrabarti et al. (1985), Mol. Cell Biol. 5:3403.

Chang et al. (1977), Nature 198:1056.

Clewell et al. (1969), Proc. Natl. Acad. Sci. USA 62:1159.

Clewell (1972), J. Bacteriol. 110:667.

Cohen (1972), Proc. Natl. Acad. Sci. USA 69:2110.

Cregg et al. (1985), Mol. Cell. Biol. 5:3376.

Das et al. (1984), J. Bacteriol 158:1165.

Davidow et al. (1985), Curr. Genet. 10:39.

De Louvencourt et al. (1983), J. Bacteriol. 154:737.

de Boer et al. (1983), Proc. Natl. Acad. Sci. USA 80:21.

Eberle et al. (1984), J. gen. Virol. 65:1839.

Gleeson et al. (1986), J. Gen. Microbiol 132:3459.

Graham and Van der Eb (1978), Virology 52:546.

Goeddel et al. (1980), Nucl. Acids Res. 8:4057.

Hess et al. (1968), J. Adv. Enzyme Reg. 7:149.

Holland (1981), J. Biol. Chem. 256:1385.

Hinnen et al. (1978), J. Adv. Enzyme Reg. 7:1929.

Ju (1987), in GENE TRANSFER VECTORS FOR MAMMALIAN CELLS (Miller and Calos, eds., Cold Spring Harbor Laboratory, Cold Spring Harbor, N.Y.)

Kunze et al. (1985), J. Basic Microbiol 25:141.

Kurtz et al. (1986), Mol. CellBiol 6:142.

Luckow and Summers (1989), Virology 17:31.

Mackett et al. (1984), J. Virol. 49:857.

Mackett et al. (1987) in "DNA Cloning", Vol. II. IRL Press, p. 191.

Maniatis et al. (1989) MOLECULAR CLONING; A LABORATORY MANUAL, Second Edition (Cold Spring Harbor Press, Cold Spring Harbor, N.Y.).

Messing et al. (1981), Nucleic Acids. Res. 9:309.

McGeoch et al. (1988), J. gen Virol. 69:1531.

McLean et al. (1982), J. gen Virol. 63:297.

Michelle et al., Int. Symposium on Viral Hepatitis.

Moss (1987), in GENE TRANSFER VECTORS FOR MAMMALIAN CELLS (Miller and Calos, eds., Cold Spring Harbor Laboratory, Cold Spring Harbor, N.Y.) p. 10.

Neurath et al. (1984), Science 224:392.

Pellett et al. (1985), Proc. Natl. Acad. Sci. U.S.A. 82: 5870.

Sanger et al. (1977), Proc. Natl. Acad. Sci USA 74:5463.

Shimatake et al. (1981), Nature 292:128

Smith et al. (1983), Mol. & Cell Biol. 3:2156.

Spear and Roizman (1972), J. Virol. 9:143.

Triezenberg et al. (1988), Genes and Development 2:718.

Valenzuela et al. (1982), Nature 298:344.

Valenzuela et al. (1984), in HEPATITIS B (Millman, I. et al., ed. Plenum Press) p225.

Warner (1984), DNA 3:401.

Watson et al. (1982), Science 218:381.

Weissman (1981), "The cloning of interferon and other mistakes." In Interferon 3 (ed. I. Gresser).

Zoller (1982), Nucleic Acids Res. 10:6487.

DISCLOSURE OF THE INVENTION

The instant invention results from the discovery that a tegument polypeptide of HSV, VP16, is immunogenic and ameliorates the disease caused by HSV infection. Thus, the invention includes compositions which are comprised of an immunogenic epitope of HSV VP16 which are useful for the treatment of HSV infection, polypeptides used in these compositions, methods of treating HSV infection using these compositions, and methods of preparing these compositions and immunogenic polypeptides used in these compositions; also included are vectors comprised of polynucleotide sequences encoding these polypeptides, and cells transformed with the vectors.

Accordingly, one aspect of the invention is a composition for treatment of an individual for herpes simplex virus (HSV) infection comprising an isolated immunogenic polypeptide containing an immunogenic epitope of HSV VP16, wherein the polypeptide is present in a pharmacologically effective dose in a pharmaceutically acceptable excipient.

Another aspect of the invention is a composition comprised of recombinant vaccinia virus, wherein the virus is comprised of a sequence encoding an immunogenic polypeptide selected from HSV VP16, truncated HSV VP16, and mutants thereof, wherein the polynucleotide encoding the immunogenic polypeptide is operably linked to a control sequence.

Yet another aspect of the invention is a method of producing a composition for treatment of HSV infection comprising:

(a) providing an immunogenic polypeptide comprised of an immunogenic epitope of HSV VP16;

(b) formulating the polypeptide in a pharmaceutically acceptable excipient.

Another aspect of the invention is a composition produced by the above method.

Still another aspect of the invention is a method of treating an individual for HSV infection comprising administering to the individual the above-described compositions.

An additional aspect of the invention is a recombinant polynucleotide encoding a polypeptide comprised of an immunogenic epitope of HSV-2 VP16.

Yet another aspect of the invention is a recombinant vector comprised of the above-described polynucleotide.

Yet another aspect of the invention is a recombinant expression system comprising an open reading frame (ORF) of DNA encoding a polypeptide comprised of an immunogenic epitope of HSV-2 VP16, wherein the ORF is operably linked to a control sequence compatible with a desired host.

Another aspect of the invention is a host cell transformed with the recombinant expression system of claim 38.

Still another aspect of the invention is a method of producing an immunogenic polypeptide for use in the treatment of HSV infection, the method comprising:

(a) providing the above-described host cell;

(b) incubating the host cell under conditions which allow expression of the polypeptide; and (c) isolating the expressed polypeptide from the host cell.

Still another aspect of the invention is an immunogenic polypeptide for use in the treatment of HSV infection, produced by the above-described method.

BRIEF DESCRIPTION OF THE DRAWINGS

FIG. 1 is a schematic drawing of an HSV virion.

FIG. 2 shows the putative amino acid sequences of HSV-1 VP16 and HSV-2 VP16.

FIGS. 3A-1 through 3A-3 and 3B-1 through 3B-2 show the nucleotide sequence encoding HSV-2 VP16, and the amino acids encoded therein.

Figure 6A:
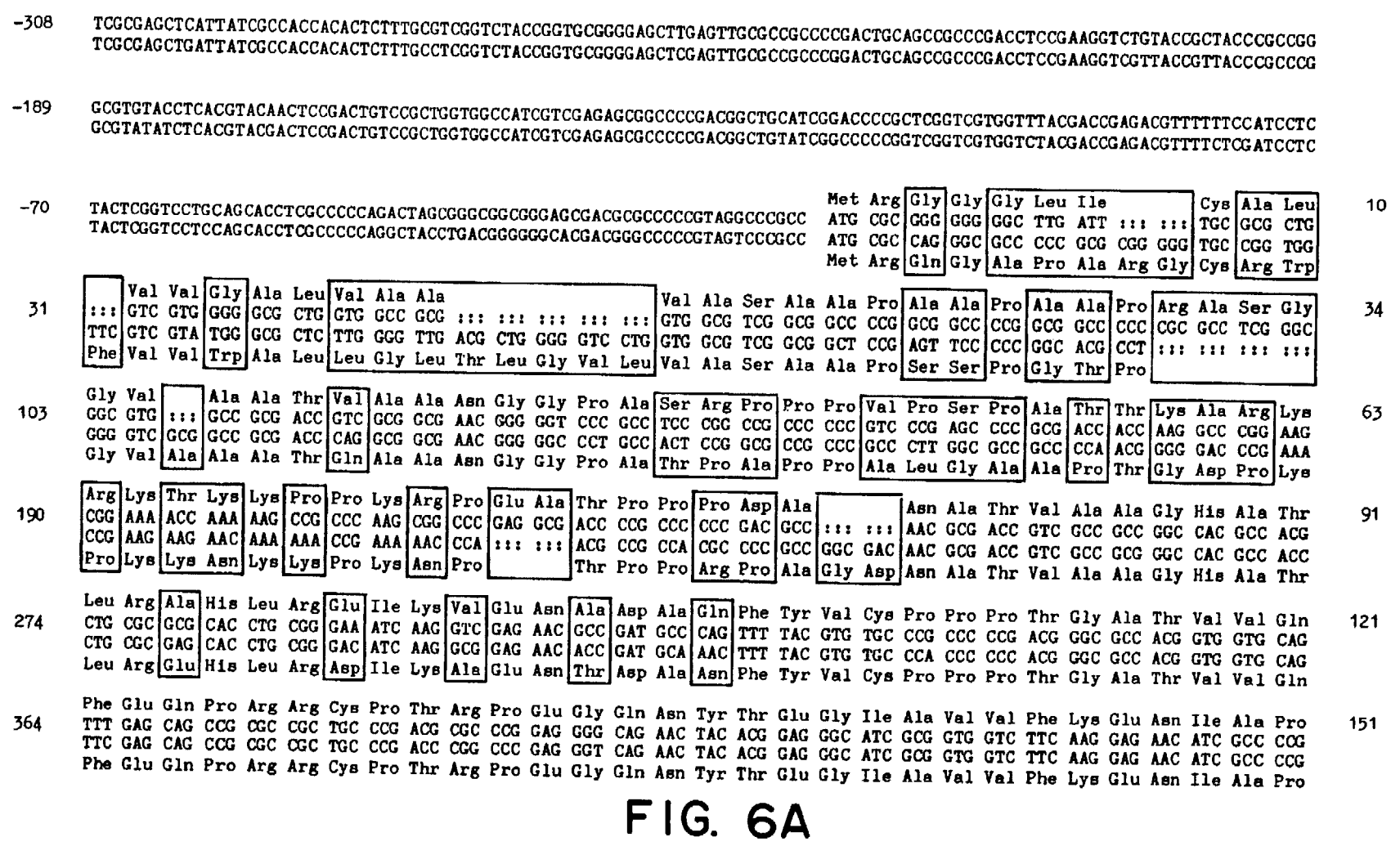
Figure 6B:
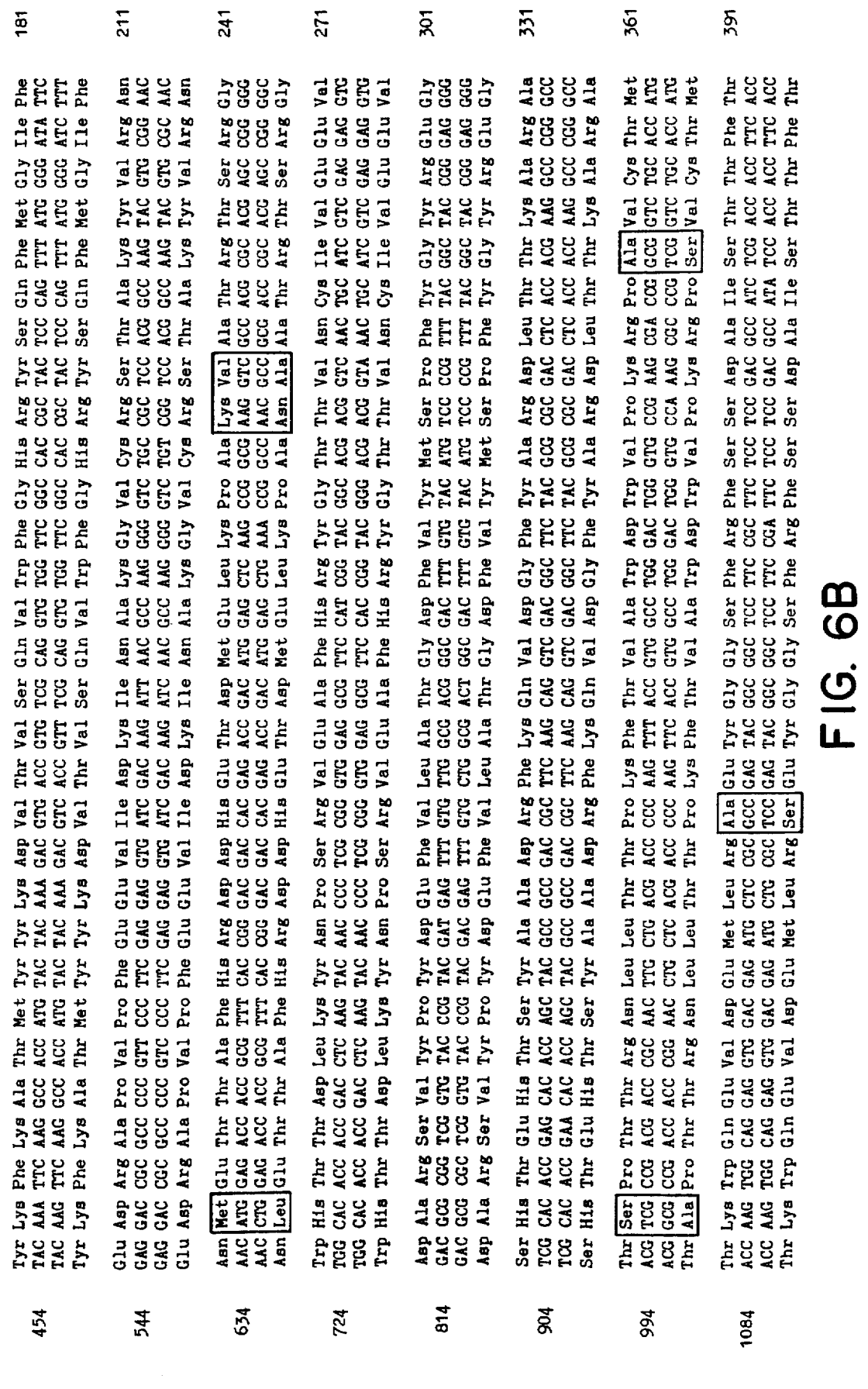
Figure 6C:
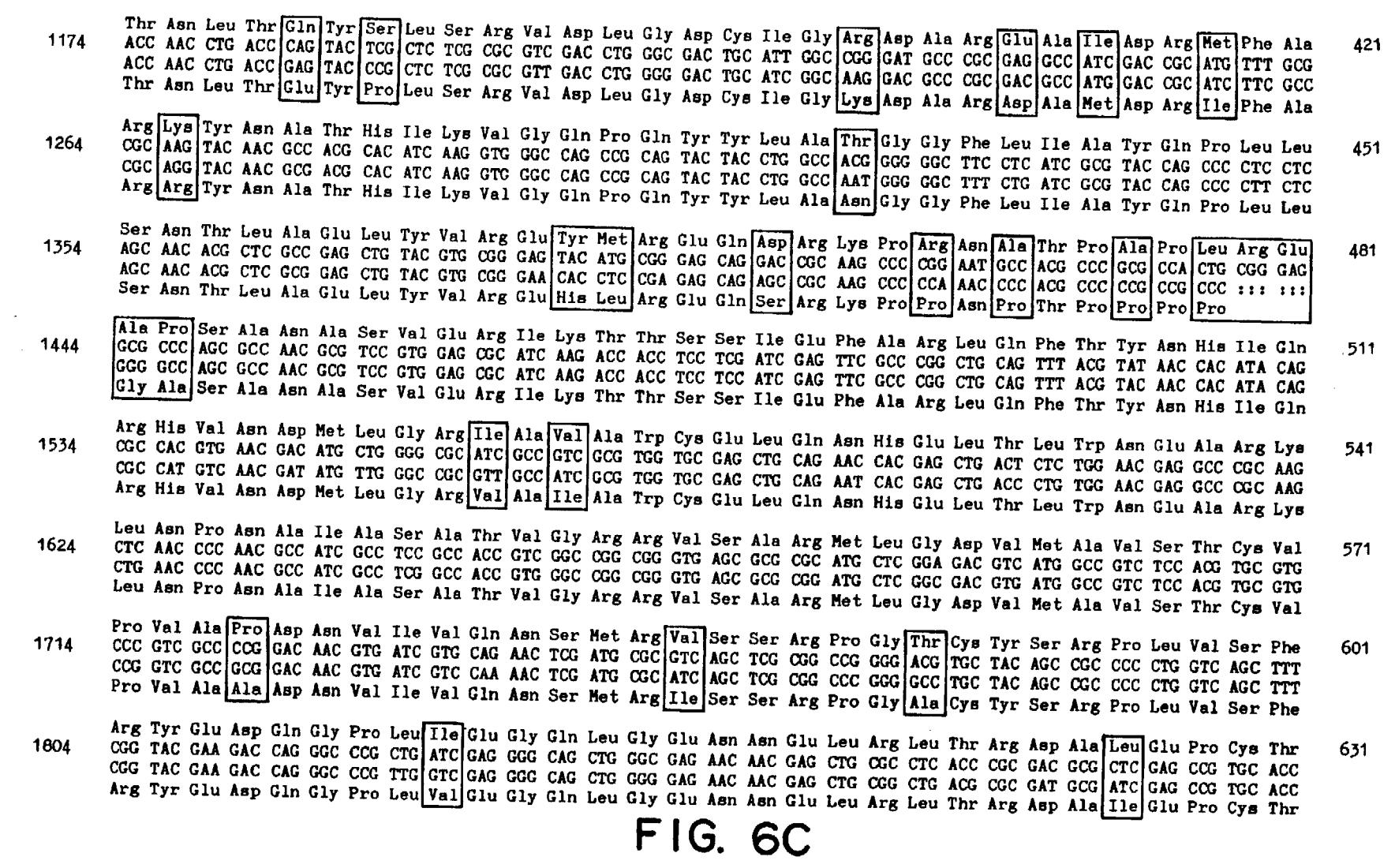
Figure 6D:
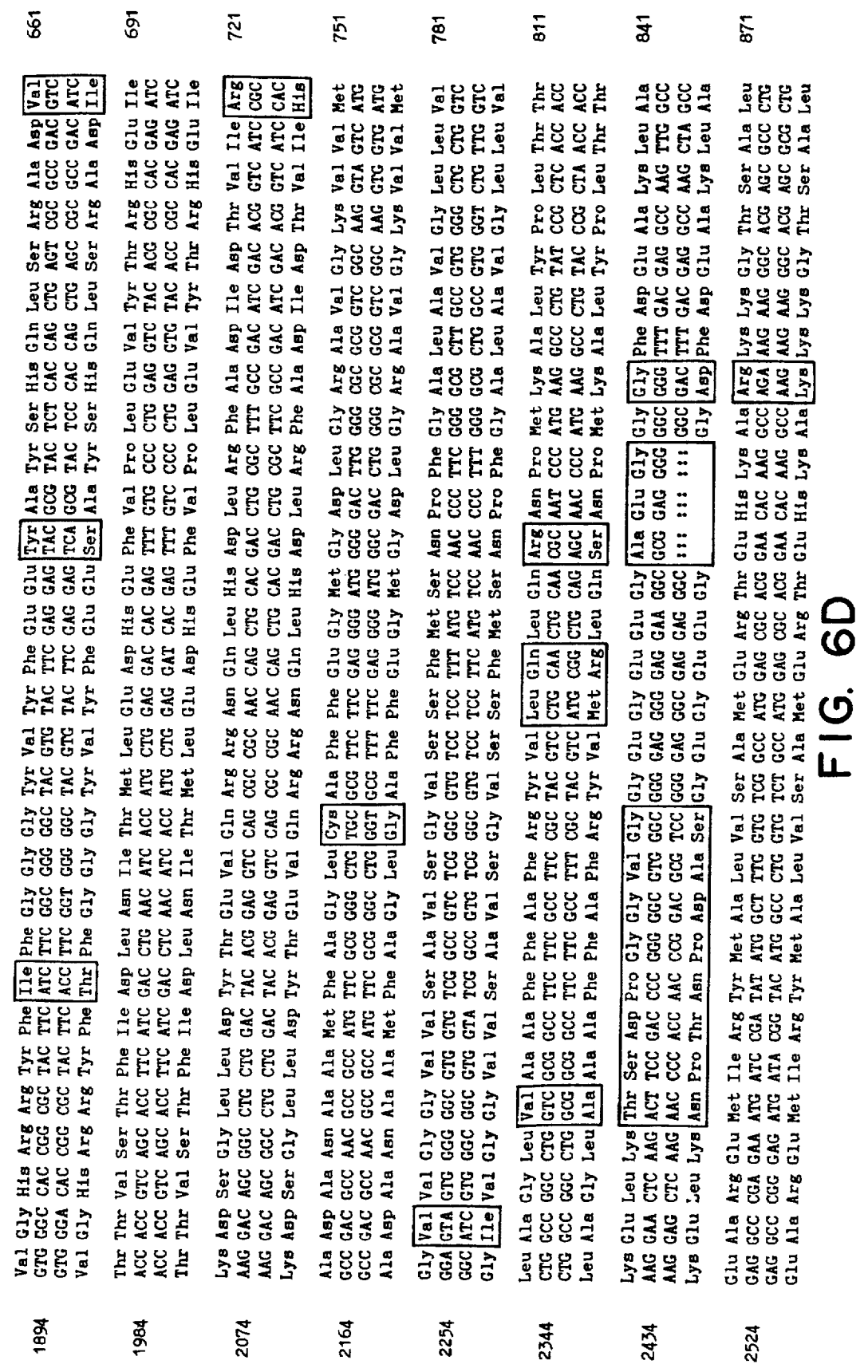
Figure 6E:
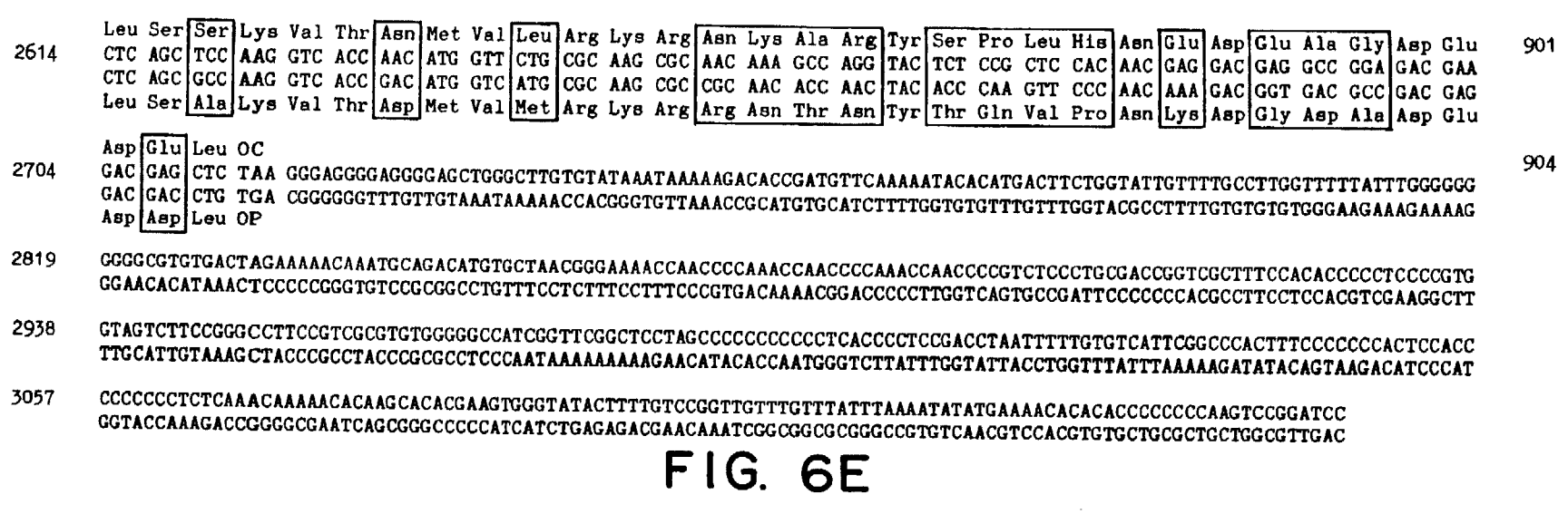

FIGS. 6A through 6E are of FIG. 4 of WO88/02634, which presents the nucleotide sequence encoding HSV gB2, and the amino acids encoded therein.

MODES FOR CARRYING OUT THE INVENTION

Figure 4:
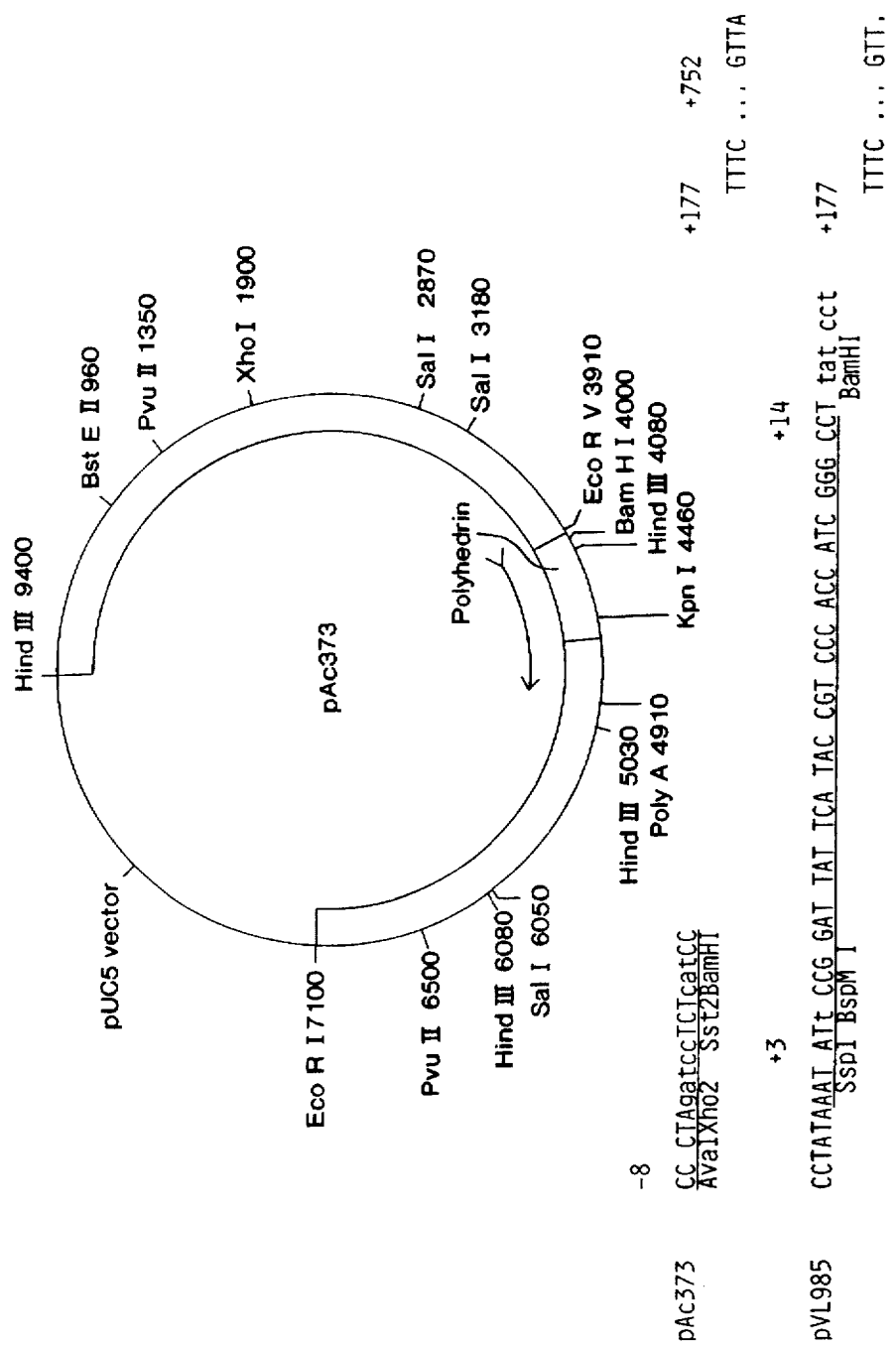
FIG. 4 is a map showing some significant features of the vector pAC373, of pVL985, and the sequence encoding the n-terminal amino acids of the polyhedrin gene.

The following terminology is used herein.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example,unnatural amino acids, etc.), polypeptides with substituted linkages, as well as other modifications known in the art, both naturally occurring and non-naturally occurring.

The term "isolated polypeptide" refers to a polypeptide which is substantially free of other HSV viral components, particularly polynucleotides. A polypeptide composition is "substantially free" of another component if the weight of the polypeptide in the composition is at least 70% of the weight of the polypeptide and other component combined, more preferably at least about 80%, still more preferably about 90%, and most preferably 95% or greater. For example, a composition containing 100 µg/mL VP16 and only 3 µg/mother HSV components (e.g., DNA, lipids, etc.) is substantially free of "other HSV viral components," and thus is a composition of an isolated polypeptide within the scope of this definition. Similarly, some compositions of the invention comprise an isolated VP16 polypeptide in combination with one or more isolated HSV glycoproteins, e.g., gB, gC, gD, and the like.

A "recombinant polynucleotide" intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, etc.), those containing alkylators, those with modified linkages (e.g., alpha anomeric nucleic acids, etc.), as well as unmodified forms of the polynucleotide.

"Recombinant host cells", "host cells", "cells", "cell lines", "cell cultures", and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

A "replicon" is any genetic element, e.g., a plasmid, a chromosome, a virus, a cosmid, etc., that behaves as an autonomous unit of polynucleotide replication within a cell; i.e., capable of replication under its own control.

A "vector" is a replicon further comprising sequences providing replication and/or expression of the open reading frame.

"Control sequence" refers to polynucleotide sequences which are necessary to effect the expression of coding sequences to which they are ligated. The nature of such control sequences differs depending upon the host organism: in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences which govern secretion.

A "promoter" is a nucleotide sequence which is comprised of consensus sequences which allow the binding of RNA polymerase to the DNA template in a manner such that mRNA production initiates at the normal transcription initiation site for the adjacent structural gene.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at about 8 to 10 such amino acids. Methods of determining the spatial conformation of such amino acids are known in the art, and include, for example, x-ray crystallography and 2-dimensional nuclear magnetic reference.

An "immunogenic epitope" is an epitope in a polypeptide that elicits a cellular and/or humoral immune response; the response may be elicited by the polypeptide alone, or may require the presence of a carrier in the presence or absence of an adjuvant.

An epitope is the "immunologic equivalent" of another epitope in a designated polypeptide when it has the amino acid sequence and conformation which allows it to cross-react with antibodies which bind immunologically to the epitope in the designated polypeptide.

As used herein, an epitope of a designated polypeptide denotes epitopes with the same amino acid sequence as the epitope in the designated polypeptide, and immunologic equivalents thereof.

A polypeptide which is "comprised of an immunogenic epitope of HSV VP16" is a polypeptide which contains a sequence of amino acids of HSV VP16 of at least the number to form the immunogenic epitope, usually at least about five amino acids, more usually at least about 8 amino acids, and even more usually about 10 or more amino acids; the maximum size is not critical. The amino acid sequence from HSV VP16 may be linked at the amino terminus and/or carboxy terminus to another polypeptide (e.g., a carrier protein), either by covalent attachment or by expressing a fused polynucleotide to form a fusion protein. If desired, one may insert or attach multiple repeats of the epitope, and/or incorporate a variety of epitopes. The carrier protein may be derived from any source, but will generally be a relatively large, immunogenic protein such as BSA, KLH, or the like. If desired, one may employ a substantially full-length VP16 protein as the carrier, multiplying the number of immunogenic epitopes. Alternatively, the amino acid sequence from HSV VP16 may be linked at the amino terminus and/or carboxy terminus to a non-HSV VP16 amino acid sequence, thus the polypeptide would be a "fusion polypeptide". Analogous types of polypeptides may be constructed using epitopes from other designated viral proteins.

A "mutant" of a designated polypeptide refers to a polypeptide in which the amino acid sequence of the designated polypeptide has been altered by the deletion or substitution of one or more amino acids in the sequence, or by the addition of one or more amino acids to the sequence. Methods by which mutants occur (for example, by recombination) or are made (for example, by site directed mutagenesis) are known in the art.

"Transformation" refers to the insertion of an exogenous polynucleotide into a host cell, irrespective of the method used for the insertion, for example, direct uptake, transduction (including viral infection), f-mating or electroporation. The exogenous polynucleotide may be maintained as a non-integrated vector, for example, a plasmid or viral genome, or alternatively, may be integrated into the host genome.

An "individual" refers to a vertebrate, particularly a member of a mammalian species, and includes but is not limited to domestic animals, sports animals, and primates, including humans.

As used herein, "treatment" refers to any of (i) the prevention of infection or reinfection, as in a traditional vaccine, (ii) the reduction or elimination of symptoms, and (iii) the substantial elimination of the virus. Treatment may be effected prophylactically (before or prior to infection) or therapeutically (during or following infection).

The term "effective amount" refers to an amount of epitope-bearing polypeptide sufficient to induce an immune response in the subject to which it is administered. The immune response may comprise, without limitation, induction of cellular and/or humoral immunity. Preferably, the effective amount is sufficient to effect treatment, as defined above. The exact amount necessary will vary from subject to subject, depending on the species, age, and general condition of the subject, the severity of the condition being treated, the particular polypeptide selected and its mode of administration, etc. Thus, it is not possible to specify an exact effective amount. However, the appropriate effective amount may be determined by one of ordinary skill in the art using only routine experimentation.

The term "HSV glycoprotein" refers to any of the glycoproteins found in the membrane region of HSV-1, HSV-2, and related herpes viruses. Presently preferred HSV glycoproteins are gB, gC, gD, and gE. Included within this definition are glycoproteins extracted from natural viruses (e.g., from infected sera or cell culture) and glycoproteins produced by recombinant methods. Such glycoproteins may be modified, either by chemical or enzymatic means (e.g., by proteolytic cleavage, deglycosylation, etc.), or by mutation, or by recombinant DNA techniques (e.g., by fusing HSV glycoprotein genes with other genes to provide fusion proteins, or by deleting or replacing sections of DNA sequence).

The practice of the present invention will employ, unless otherwise indicated, conventional techniques of molecular biology, microbiology, biochemistry, and immunology, which are within the skill of the art. Such techniques are explained fully in the literature. See, e.g., Sambrook, Maniatis, & Fitsch, MOLECULAR CLONING, A LABORATORY MANUAL, Second Edition (1989); DNA CLONING, VOLUMES I and II (D. N. Glover, Ed. 1985); OLIGONUCLEOTIDE SYNTHESIS (M. J. Gait Ed. (1984); NUCLEIC ACID HYBRIDIZATION (B. D. Hames & S. J. Higgins eds. 1984); ANIMAL CELL CULTURE (R. I. Freshney ed. 1986); IMMOBILIZED CELLS AND ENZYMES (IRL Press, 1986; B. Perbal, A PRACTICAL GUIDE TO MOLECULAR CLONING (1984); the series, METHODS IN ENZYMOLOGY (Academic Press, Inc.), and particularly Vol. 154 and Vol. 155 (Wu and Grossman, and Wu, eds., respectively); GENE TRANSFER VECTORS FOR MAMMALIAN CELLS (J. H. Miller and M. P. Calos eds. 1987, Cold Spring Harbor Laboratory), IMMUNOCHEMICAL METHODS IN CELL AND MOLECULAR BIOLOGY (Academic Press, London), Scopes, (1987); PROTEIN PURIFICATION: PRINCIPLES AND PRACTICE, Second Edition (Springer-Verlag, N.Y.), and HANDBOOK OF EXPERIMENTAL IMMUNOLOGY, Volumes I–IV, (D. M. Weir and C. C. Blackwell, eds., 1986.) All patents, patent applications, and publications mentioned herein, both supra and infra, are hereby incorporated herein by reference.

Compositions of the invention, which are used to treat individuals for HSV infection, are comprised of a polypeptide which contains one or more immunogenic epitopes of HSV VP16. The surprising result that HSV VP16 is immunogenic, and protective, is demonstrated in Examples 4 and 5, infra. Thus, the compositions comprised of polypeptides containing at least one immunogenic epitope of HSV VP16, may be used for treatment of individuals to prevent or lessen the disease symptoms associated with HSV infections. Moreover, the results also show that the addition of an HSV glycoprotein to the vaccine which is comprised of HSV VP16 enhances both the immunogenic and protective effect. Therefore, in a preferred mode, the vaccines are further comprised of at least one immunogenic epitope of an HSV glycoprotein. The glycoprotein epitope may exist on the same polypeptide as the VP16 epitope, or may exist on a second polypeptide. In a more preferred mode, the glycoprotein epitope is from HSV gB or HSV gD.

In order to prepare the vaccine, a polypeptide comprised of one or more immunogenic epitopes of HSV VP16 is provided. If an immunogenic epitope of an HSV glycoprotein is also desired in the vaccine it may also be included in the polypeptide comprised of the HSV VP16 epitope, or alternatively, it may be provided in a second polypeptide.

The provided polypeptides may be full-length HSV VP16 and/or HSV glycoproteins. If the provided polypeptides are full length, they may be isolated from the virus. Isolation and further purification may be accomplished by techniques known in the art. See, for example, Methods in Enzymology, and Scopes, PROTEIN PURIFICATION, which discuss a variety of methods for purifying proteins.

Alternatively, the full length polypeptides may be synthesized using recombinant DNA techniques and either the known sequences which encode the glycoproteins and the HSV-1 VP16, or the sequence for HSV-2 VP16 provided herein. The full length polypeptides may contain one or more substitutions in the amino acid sequence, as long as the immunogenicity of the designated polypeptide is still evident.

The invention also contemplates the use of polypeptides comprised of truncated HSV VP16 and/or glycoprotein amino acid sequences. The size of polypeptides comprising the truncated HSV VP16 sequences or glycoprotein sequences can vary widely, the minimum size being a sequence of sufficient size to provide the desired immunogenic epitope, while maximum size is not critical. For convenience, the maximum size usually is not substantially greater than that required to provide the desired epitopes and function(s) of the heterologous sequence, if any. Typically, the truncated HSV amino acid sequence will range from about 5 to about 400 amino acids in length. More typically, however, the viral sequence containing the immunogenic epitope will be a maximum of about 100 amino acids in length, preferably a maximum of about 50 amino acids.

Truncated HSV VP16 or HSV glycoprotein amino acid sequences which are immunogenic can be identified in a number of ways. For example, the entire viral protein sequence can be screened by preparing a series of short peptides that together span the entire protein sequence. By starting with, for example, 100 mer polypeptides, it would be routine to test each polypeptide for the presence of epitope(s) showing a desired reactivity, and then testing progressively smaller and overlapping fragments from an identified 100 mer to map the epitope of interest. Screening such peptides in an immunoassay is within the skill of the art, and appropriate immunoassays for immunogenicity are described in the Examples. Methods of computer analysis of a protein sequence to identify potential epitopes are also known. For example, putative epitopes of HSV-2 VP16 have been determined from the putative amino acid sequence shown in FIG. 2, using as criteria the surface probability, antigen index, hydrophilicity, charge, or lack of overt structure of the regions of the HSV-2 VP16 polypeptide. These putative epitopes are located at about amino acid (aa) 15 to about aa 34; at about aa 193 to about aa 220; at about aa 320 to about aa 330; at about aa 360 to about aa 371; at about aa 378 to about aa 390; at about aa 400 to about aa 410; and at about aa 480 to about aa 490. After the identification of putative epitopes, oligopeptides comprising the identified regions can be prepared for screening.

If desired, a single polypeptide may include at least one truncated HSV VP16 sequence which includes an immunogenic epitope, and also, at least one truncated HSV glycoprotein sequence which includes an immunogenic epitope. Alternatively, the truncated HSV VP16 and HSV glycoprotein sequences may be on separate polypeptides. While truncated sequences can be produced by various known treatments of the subject native viral protein(s), it is generally preferred to make synthetic or recombinant polypeptides comprised of the desired immunogenic epitopes.

Recombinant polypeptides comprised of the truncated HSV VP16 sequences can be made up entirely of VP16 sequences (one or more epitopes, either contiguous or noncontiguous), or VP16 sequence or sequences in a fusion protein. Similarly, polypeptides comprised of truncated HSV glycoprotein sequences can be made up entirely of the glycoprotein sequence (one or more epitopes, either contiguous or noncontiguous), or the glycoprotein sequence or sequences in a fusion protein.

In fusion proteins, useful heterologous sequences include sequences that provide for secretion from a recombinant host, enhance the immunological reactivity of the VP16 or glycoprotein epitope(s), or facilitate the coupling of the polypeptide to a support or a vaccine carrier. See, e.g., EPO Pub. No. 116,201; U.S. Pat. No. 4,722,840; EPO Pub. No. 259,149; U.S. Pat. No. 4,629,783, the disclosures of which are incorporated herein by reference.

Full length as well as polypeptides comprised of truncated HSV VP16 and/or HSV glycoprotein sequences, and mutants thereof, may be prepared by recombinant technology. A DNA sequence putatively encoding HSV-1 VP16 (also known as VmW65) is disclosed in Campbell et al (1984), the disclosure of which is incorporated herein by reference. A DNA sequence encoding HSV-2 VP16, discovered by the herein inventors and described in Example 1, is provided in FIG. 3, infra. In the figure, the Met indicated by the arrow is the putative initiating methionine. The method for the provision of the sequence of HSV-2 VP16 is simply of historical interest, since the information in the sequence data is available both in FIG. 3 and in ATCC Deposit No. 68,372, which is incorporated herein by reference. The sequences encoding a number of HSV glycoproteins, including gB and gD are known. For example, sequences encoding HSV-1 and HSV-2 gB are shown in U.S. Pat. No. 4,642,333; sequences encoding HSV gD are described in Watson et al. (1982). Methods for expressing gB and gD, and fragments thereof, are described in WO88/02634. The availability of these sequences permits the construction of polynucleotides encoding immunogenic regions of the HSV VP16 polypeptides and HSV glycoproteins.

Polynucleotides encoding the desired polypeptide comprised of one or more of the immunogenic HSV VP16 epitopes and/or one or more of the immunogenic glycoprotein epitopes may be chemically synthesized or isolated, and inserted into an expression vector. The vectors may or may not contain portions of fusion sequences such as beta-Galactosidase or superoxide dismutase (SOD). Methods and vectors which are useful for the production of polypeptides which contain fusion sequences of SOD are described in European Patent Office Publication number 0196056, published Oct. 1, 1986.

The DNA encoding the desired polypeptide, whether in fused or mature form and whether or not containing a signal sequence to permit secretion, may be ligated into expression vectors suitable for any convenient host. The hosts are then transformed with the expression vector. Both eukaryotic and prokaryotic host systems are presently used in forming recombinant polypeptides, and a summary of some of the more common control systems and host cell lines is presented infra. The host cells are incubated under conditions which allow expression of the desired polypeptide. The polypeptide is then isolated from lysed cells or from the culture medium and purified to the extent needed for its intended use.

The general techniques used in extracting the genome from a virus, preparing and probing DNA libraries, sequencing clones, constructing expression vectors, transforming cells, performing immunological assays such as radioimmunoassays and ELISA assays, for growing cells in culture, and the like, are known in the art and laboratory manuals are available describing these techniques. However, as a general guide, the following sets forth some sources currently available for such procedures, and for materials useful in carrying them out.

Synthetic oligonucleotides may be prepared using an automated oligonucleotide synthesizer as described by Warner (1984). If desired, the synthetic strands may be labeled with $^{32}$P by treatment with polynucleotide kinase in the presence of $^{32}$P-ATP, using standard conditions for the reaction.

In order to create mutants, or to create desired functional sequences or to remove them, (e.g., restriction enzyme sites) DNA sequences, including those isolated from clones, may be modified by known techniques, including for example, site directed mutagenesis, as described by Zoller (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the page, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

Generally, in hybridization analysis, the DNA to be probed is immobilized on nitrocellulose filters, denatured, and prehybridized with a buffer containing 0–50% formamide, 0.75M NaCl, 75 mM Na citrate, 0.02% (wt/v) each of bovine serum albumin, polyvinyl pyrollidone, and Ficoll, 50 mM Na phosphate (pH 6.5), 0.1% SDS, and 100 µg/ml carrier denatured DNA. The percentage of formamide in the buffer, as well as the time and temperature conditions of the prehybridization and subsequent hybridization steps and wash depends on the stringency required. Oligomeric probes which require lower stringency conditions are generally used with low percentages of formamide, lower temperatures, and longer hybridization times. Probes containing more than 30 or 40 nucleotides such as those derived from cloned DNAs generally employ higher temperatures, e.g., about 40°–42° C., and a high percentage, e.g., 50% formamide. Following prehybridization, labeled probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

Vector construction employs techniques which are known in the art. Site-specific DNA cleavage is performed by treating with suitable restriction enzymes under conditions which generally are specified by the manufacturer of these commercially available enzymes. In general, about 1 µg of plasmid or DNA sequence is cleaved by 1 unit of enzyme in about 20 µl buffer solution by incubation of 1–2 hr at 37° C. After incubation with the restriction enzyme, protein is removed by extraction (e.g., with phenol/chloroform), and the DNA recovered (e.g., by precipitation with ethanol). The cleaved fragments may be separated, e.g., using gel electrophoresis techniques or by sedimentation, according to the general procedures found in Methods in Enzymology (1980) 65:499–560.

Sticky ended cleavage fragments may be blunt ended using E. coli DNA polymerase I (Klenow) in the presence of the appropriate deoxynucleotide triphosphates (dNTPs) present in the mixture. Treatment with a single stranded nuclease (e.g., S1 nuclease) may also be used to hydrolyze any single stranded DNA portions.

Ligations may be carried out using standard buffer and temperature conditions using T4DNA ligase and ATP. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are used to transform suitable cloning hosts which are known in the art, e.g., E. coli, and successful transformants are selected by an appropriate marker, for example, antibiotic resistance, and screened for the correct construction.

In order to verify constructions, ligation mixtures are transformed into a suitable host, e.g., E. coli HB101, and successful transformants selected by antibiotic resistance or other markers. Plasmids from the transformants are then prepared according to the method of Clewell et al. (1969), usually following chloramphenicol amplification (Clewell (1972)). The DNA is isolated and analyzed, usually by restriction enzyme analysis and/or sequencing. Sequencing may be by the dideoxy method of Sanger et al. (1977), as further described by Messing et al. (1981), or by the method of Maxam et al. (1980). Problems with band compression, which are sometimes observed in GC rich regions, may be overcome by use of T-deazoguanosine according to Barr et al. (1986).

Transformation of the vector containing the desired sequence into the appropriate host may be by any known method for introducing polynucleotides into a host cell, including, for example, packaging the polynucleotide in a virus and transducing the host cell with the virus, or by direct uptake of the polynucleotide. The transformation procedure used depends upon the host to be transformed. For example, in vivo transformation using vaccinia virus as the transforming agent for polynucleotides encoding HSV-2 VP16 is described infra., in the Examples. Transformation may also be accomplished in vitro systems. Bacterial transformation by direct uptake generally employs treatment with calcium or rubidium chloride (Cohen (1972); Sambrook (1989)). Yeast transformation by direct uptake may be carried out using the method of Hinnen et al. (1978). Mammalian transformations by direct uptake may be conducted using the calcium phosphate precipitation method of Graham and Van der Eb (1978), or the various known modifications thereof. Other methods for the introduction of recombinant polynucleotides into cells, particularly into mammalian cells, which are known in the art include dextran mediated transfection, calcium phosphate mediated transfection, polybrene mediated transfection, protoplast fusion, electroporation, encapsulation of the polynucleotide(s) in liposomes, and direct microinjection of the polynucleotides into nuclei.

In order to obtain expression of desired coding sequences, host cells are transformed with polynucleotides (which may be expression vectors), which are comprised of control sequences operably linked to the desired coding sequences. The control sequences are compatible with the designated host. Among prokaryotic hosts, E. coli is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. Promoter sequences may be naturally occurring, for example, the β-lactamase (penicillinase) (Weissman (1981)), lactose (lac)(Chang et al. (1977), and tryptophan (trp)(Goeddel et al. (1980)), and lambda-derived P<sub>L</sub> promoter system and N gene ribosome binding site (Shimatake et al. (1981)). In addition, synthetic promoters which do not occur in nature also function as bacterial promoters. For example, transcription activation sequences of one promoter may be joined with the operon sequences of another promoter, creating a synthetic hybrid promoter (e.g., the tac promoter, which is derived from sequences of the trp and lac promoters (De Boer et al. (1983)). The foregoing systems are particularly compatible with *E. coli*; if desired, other prokaryotic hosts such as strains of Bacillus or Pseudomonas may be used, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach et al. (1983)), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al. (1968)); for example, alcohol dehydrogenase (ADH)(E.P.O. Publication No. 284044), enolase, glucokinase, glucose-6-phosphate isomerase, glyceraldehyde-3-phosphate dehydrogenase (GAP or GAPDH), hexokinase, phosphofructokinase, 3-glycerophosphate mutase, and pyruvate kinase (PyK)(E.P.O. Publication No. 329203). The yeast PHO5 gene, encoding acid phosphatase, also provides useful promoter sequences (Miyanohara et al. (1983). In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (E.P.O. Publication No. 164556). Furthermore, a yeast promoter can include naturally occurring promoters of non-yeast origin that have the ability to bind yeast RNA polymerase for the appropriate initiation of transcription.

Other control elements which may be included in the yeast expression vector are terminators (e.g., from GAPDH, and from the enolase gene (Holland (1981)), and leader sequences. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (E.P.O. Publication No. 12,873) and the α-factor gene (U.S. Pat. No. 4,588,684). Alternatively, leaders of non-yeast origin, such as an interferon leader, also provide for secretion in yeast (E.P.O. Publication No. 60057). A preferred class of secretion leaders are those that employ a fragment of the yeast α-factor gene, which contains both a "pre" signal sequence, and a "pro" region. The types of α-factor fragments that can be employed include the full-length pre-pro α-factor leader, as well as truncated α-factor leaders (U.S. Pat. Nos. 4,546,083 and 4,870,008; E.P.O. Publication No. 324274. Additional leaders employing an α-factor leader fragment that provides for secretion include hybrid α-factor leaders made with a pre-sequence of a first yeast, but a pro- region from a second yeast α-factor. (See, e.g., P.C.T. WO 89/02463).

Expression vectors, either extrachromosomal replicons or integrating vectors, have been developed for transformation into many yeasts. For example, expression vectors have been developed for *Candida albicans* (Kurtz et al. (1986)), *Candida maltosa* (Kunze et al. (1985)), *Hanzenula polymorpha* (Gleeson et al. (1986)), *Kluyveromyces fragilis* (Das et al. (1984)), *Kluyveromyces lactis* (De Louvencourt et al. (1983)), *Pichia guillerimondii*, (Kunze et al. (1985)), *Pichia pastoris* (Cregg et al. (1985); U.S. Pat. Nos. 4,837,148 and 4,929,555)), *Schizosaccharomyces pombe* (Beach and Nurse (1981)), and *Yarrowia lipolytica* (Davidow et al. (1985)).

Mammalian cell lines available as hosts for expression are known in the art and include many immortalized cell lines available from the American Type Culture Collection (ATCC), including, for example, HeLa cells, Chinese hamster ovary (CHO) cells, baby hamster kidney (BHK) cells, COS monkey cells, and a number of other cell lines. Suitable promoters for mammalian cells are also known in the art and include viral promoters such as that from Simian Virus 40 (SV40), Rous sarcoma virus (RSV), adenovirus (ADV) and bovine papilloma virus (BPV) (See, Sambrook (1989) for examples of suitable promoters). Mammalian cells may also require terminator sequences and poly A addition sequences; enhancer sequences which increase expression may also be included, and sequences which cause amplification of the gene may also be desirable. These sequences are known in the art.

Vectors suitable for replication in mammalian cells are known in the art, and may include viral replicons, or sequences which ensure integration of the appropriate sequences encoding the desired polypeptides into the host genome.

A vector which is used to express foreign DNA and which may be used in vaccine preparation is Vaccinia virus. In this case, the heterologous DNA is inserted into the Vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid vectors that greatly facilitate the construction of recombinant viruses have been described (see, for example, Mackett et al. (1984), Chakrabarti et al. (1985); Moss (1987)). Expression of the desired polypeptides comprised of immunogenic regions then occurs in cells or individuals which are infected and/or immunized with the live recombinant vaccinia virus.

Other systems for expression of polypeptides include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedrin gene promoter to drive expression of heterologous genes. Currently the most commonly used transfer vector for introducing foreign genes into AcNPV is pAc373, shown in FIG. 4. Many other vectors, known to those of skill in the art, have also been designed for improved expression. These include, for example, pVL985 (which alters the polyhedrin start codon from ATG to ATT, and which introduces a BamHI cloning site 32 basepairs downstream from the ATT; See Luckow and Summers (1989). AcNPV transfer vectors for high level expression of nonfused foreign proteins are shown in FIG. 4. In the figure, the numbers shown refer to positions within the native gene, where the A of the ATG codon is +1. FIG. 4 also shows a restriction endonuclease map of the transfer vector pAc373. The map shows that a unique BamHI site is located following position −8 with respect to the translation initiation codon ATG of the polyhedrin gene. There are no cleavage sites for SmaI, PstI, BglI, XbaI or SstI. Good expression of nonfused foreign proteins usually requires foreign genes that ideally have a short leader sequence containing suitable translation initiation signals preceding an ATG start signal. The plasmid also contains the polyhedrin polyadenylation signal and the ampicillin-resistance (amp) gene and origin of replication for selection and propagation in E. coli.

Methods for the introduction of heterologous DNA into the desired site in the baculovirus are known in the art. (See Summers and Smith, Texas Agricultural Experiment Station Bulletin No. 1555; Ju et al. (1987); Smith et al. (1983); and Luckow and Summers (1989)). For example, the insertion can be into a gene such as the polyhedrin gene, by homologous recombination; insertion can also be into a restriction enzyme site engineered into the desired baculovirus gene. The inserted sequences may be those which encode all or varying segments of HSV VP16 and/or HSV glycoprotein.

The signals for posttranslational modifications, such as signal peptide cleavage, proteolytic cleavage, and phosphorylation, appear to be recognized by insect cells. The signals required for secretion and nuclear accumulation also appear to be conserved between the invertebrate and vertebrate cells. Examples of the signal sequences from vertebrate cells which are effective in invertebrate cells are known in the art, for example, the human interleukin 2 signal (IL2$_s$) which is a signal for transport out if the cell, is recognized and properly removed in insect cells.

It is often desirable that the polypeptides prepared using the above host cells and vectors be fusion polypeptides. As with non-fusion polypeptides, fusion polypeptides may remain intracellular after expression. Alternatively, fusion proteins can also be secreted from the cell into the growth medium if they are comprised of a leader sequence fragment. Preferably, there are processing sites between the leader fragment and the remainder of the foreign gene that can be cleaved either in vivo or in vitro.

In instances wherein the synthesized polypeptide is correctly configured so as to provide the correct epitope, but is too small to be immunogenic, the polypeptide may be linked to a suitable carrier. A number of techniques for obtaining such linkage are known in the art, including the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue.) These reagents create a disulfide linkage between themselves and peptide cysteine resides on one protein and an amide linkage through the ε-amino on a lysine, or other free amino group in other amino acids. A variety of such disulfide/amide-forming agents are known. See, for example, Immun. Rev. (1982) 62:185. Other bifunctional coupling agents for a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimido-methyl) cyclohexane-1-carboxylic acid, and the like. The carboxyl groups can be activated by combining them with succinimide or 1-hydroxyl-2-nitro-4-sulfonic acid, sodium salt. Additional methods of coupling antigens employ the rotavirus/ "binding peptide" system described in EPO Publication No. 259,149. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides such as latex functionalized sepharose, agarose, cellulose, cellulose beads and the like; polymeric amino acids, such as polyglutamic acid, polylysine, and the like; amino acid copolymers; and inactive virus particles (see infra.). Especially useful protein substrates are serum albumins, keyhole limpet hemocyanin, immunoglobulin molecules, thyroglobulin, ovalbumin, tetanus toxoid, and other proteins well known to those of skill in the art.

The immunogenicity of the epitopes of HSV VP16, particularly of HSV-2 VP16, and of HSV glycoproteins, particularly HSV gB and/or HSV gD, may also be enhanced by preparing them in eukaryotic systems fused with or assembled with particle-forming proteins such as, for example, that associated with hepatitis B surface antigen. See, e.g., U.S. Pat. No. 4,722,840. Constructs wherein the HSV VP16 or glycoprotein epitope is linked directly to the particle-forming protein coding sequences produces hybrids which are immunogenic with respect to the HSV epitope. In addition, all of the vectors prepared include epitopes specific to HBV, having various degrees of immunogenicity, such as, for example, the pre-S peptide. Thus, particles constructed from particle forming protein which include HSV sequences are immunogenic with respect to HSV and HBV.

Hepatitis surface antigen (HBSAg) has been shown to be formed and assembled into particles in S. cerevisiae (Valenzuela et al. (1982), as well as in, for example, mammalian cells (Valenzuela et al. (1984)). The formation of such particles has been shown to enhance the immunogenicity of the monomer subunit. The constructs may also include the immunodominant epitope of HBSAg, comprising the 55 amino acids of the presurface (pre-S) region. Neurath et al. (1984). Constructs of the pre-S-HBSAg particle expressible in yeast are disclosed in E.P.O. Publication No. 174,444; hybrids including heterologous viral sequences for yeast expression are disclosed in E.P.O. Publication No. 175,261. These constructs may also be expressed in mammalian cells such as CHO cells using an SV40-dihydrofolate reductase vector (Michelle et al. (1984)).

In addition, portions of the particle-forming protein coding sequence may be replaced with codons encoding an HSV VP16 or HSV glycoprotein epitope. In this replacement, regions which are not required to mediate the aggregation of the units to form immunogenic particles in yeast or mammals can be deleted, thus eliminating additional HBV antigenic sites from competition with the HSV epitope(s).

The preparation of vaccines which contain an immunogenic polypeptide(s) as an active ingredient(s) is known to one skilled in the art. Typically, such vaccines are prepared as injectables, either as liquid solutions or suspensions; solid forms suitable for solution in, or suspension in, liquid prior to injection may also be prepared. the preparation may also be emulsified, or the polypeptide(s) encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include, but are not limited to: aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE, and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an HSV-VP16 epitope and/or HSV glycoprotein epitope, the antibodies resulting from administration of this polypeptide in vaccines which are also comprised of the various adjuvants.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or organic acids such as acetic, oxalic, tartaric, maleic, and the like. Salts formed with the free carboxyl groups may also be derived from inorganic bases such as, for example, sodium potassium, ammonium, calcium, or ferric hydroxides, and such organic bases as isopropylamine, trimethylamine, 2-ethylamino ethanol, histidine, procaine, and the like.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

In addition to the above, it is also possible to prepare live vaccines of attenuated microorganisms which express one or more recombinant polypeptides comprised of HSV VP16 and/or HSV glycoprotein epitopes. Suitable attenuated microorganisms are known in the art and include, for example, viruses (e.g., vaccinia virus) as well as bacteria.

The vaccines are administered in a manner compatible with the dosage formulation, and in such amount as will be prophylactically and/or therapeutically effective. The quantity to be administered, which is generally in the range of 5 µg to 250 µg of antigen per dose, depends on the subject to be treated, capacity of the subject:s immune system to synthesize antibodies, and the degree of protection desired. Precise amounts of active ingredient required to be administered may depend on the judgment of the practitioner and may be peculiar to each individual.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and/or reenforce the immune response, for example, at 1–4 months for a second dose, and if needed, a subsequent dose(s) after several months. The dosage regimen will also, at lest in part, be determined by the need of the individual and be dependent upon the judgment of the practitioner.

In addition, the vaccine containing the polypeptide comprised of an immunogenic HSV VP16 epitope may be administered in conjunction with other immunoregulatory agents, for example, immune globulins.

EXAMPLES

Example 1

Isolation and Sequencing of a Gene Encoding HSV-2 VP16

The EcoRI "L" fragment of HSV-2 strain G was inserted into pUC19 to yield pH2G512, the source of the polynucleotide which encodes HSV-2 VP16. The HSV-2 polynucleotide encoding sequence was identified by Southern blot analysis, using as probe a segment of pRB3458, which contains the sequence which encodes HSV-1 VP16. The plasmids pH2G512 and pRB3458 were obtained from Dr. P. Pellett (Center for Disease Control, Atlanta, Ga.) and Dr. B. Roizman (University of Chicago, Chicago, Ill.), respectively. The construction of pRB3458 is described in Pellet et al. (1985).

More specifically, the HSV-2 VP16 encoding polynucleotide, pH2G512 was digested with EcoRI, and EcoRI and SacI, SacII, BamHI, NcoI, and SmaI, respectively. The fragments of the digested plasmid were separated by electrophoresis on a 1% agarose gel in tris-acetate buffer. After electrophoresis, the DNA in the gel was denatured with alkali, neutralized, and transferred to a "Gene Screen Plus" membrane (Dupont NEN), using the transfer protocol described in Sambrook et al. (1989). The DNA on the membrane was hybridized with the probe overnight using the manufacturer's directions; the probe was a nick-translated 2.9 Kb EcoRI-HindIII fragment isolated from pRB3458. Results of the hybridization showed that HSV-2 VP16 is encoded in a 3.5 Kb EcoRI-SacI fragment of pH2G512. Subsequently, the VP16 encoding EcoRI-SacI fragment was isolated on a 1% agarose gel, and extracted from the gel using "Gene Clean" (Bio 101). Sequencing of the fragment was accomplished by the dideoxy method. Since HSV DNA is G-C rich (i.e., >70% G-C), sequences in areas of compressions in the sequencing gels were resolved by sequencing with Taq polymerase at 65° C. The sequence of the coding strand of the fragment, and the amino acids encoded therein, are shown in FIG. 3. In the figure, the first nucleotide of the putative initiating methionine codon is shown by an arrow.

Homologies between the putative amino acid sequences for HSV-1 VP16 and HSV-2 VP16 are shown in FIG. 2.

Example 2
Construction of a Vaccinia Virus Expression Vector Comprised of a Sequence Encoding HSV-2 VP16

Figure 5:
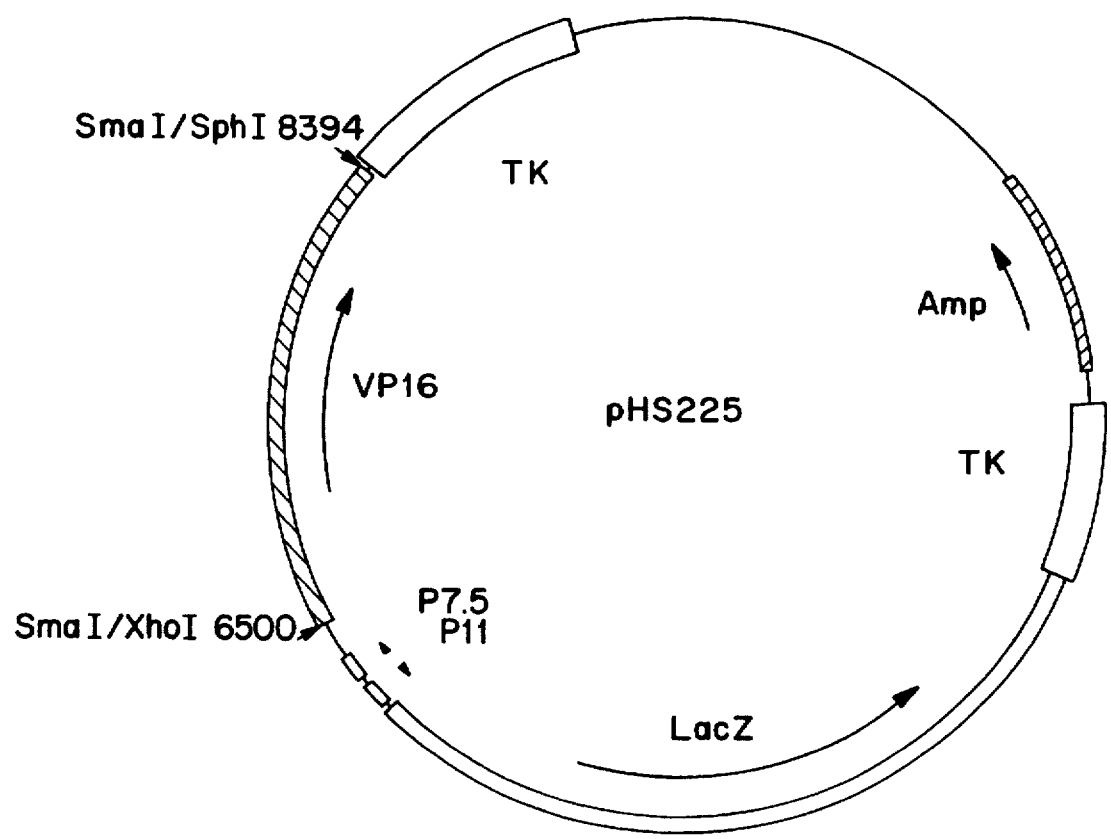
FIG. 5 is a map showing some significant features of the vector pHS225.

A vaccinia vector comprised of a sequence encoding HSV-2 VP16 was constructed as follows. Initially the VP16 encoding sequence was subcloned into the vaccinia expression vector, pSC11, to generate plasmid pHS225 (a partial map of which is shown in FIG. 5. The vector pSC11 was obtained from Dr. Bernard Moss, National Institutes of Health, Bethesda, Md. Prior to introduction of the HSV-2 VP16 coding sequence, the pSC11 vector was modified by deletion of the HindIII site in pSC11 by digestion with HindIII, followed by treatment with the Klenow fragment of DNA polymerase I, and ligation. The vector was then further modified by the introducing into the SmaI site, a polylinker containing restriction enzyme sites for SmaI, KpnI, BglII, and HindIII. The fragment containing VP16 was isolated as a 2.1 Kb XhoI-SphI fragment from pH2G512. The Xho site was filled in using the Klenow fragment of DNA polymerase I, and the SphI site was blunted using T4 DNA polymerase. The blunt-ended fragment was then ligated into the SmaI site of the modified pSC11. Vectors containing the VP16 encoding sequence were obtained by cloning; they were transformed into DH5α and transformants were selected using Ap$^r$ selection; positive clones were selected based on the presence of the appropriate size fragment after restriction enzyme analysis. One of the positive clones was named pHS225. A map showing some of the significant features of pHS225 is shown in FIG. 5.

In order to obtain a recombinant vaccinia virus vector which was suitable for expressing VP16 in individuals, the VP16 encoding sequence of pHS225 was inserted into the TK locus of wild type vaccinia strain, WR, by recombination using the Lipofectin™ (GIBCO BRL, Gaithersburg, Md.) transfection protocol described by the manufacturer of Lipofectin. Recombinant TK$^{31}$ viruses were isolated by BuDR selection, and plaque-purified using the protocol of Mackett et al. (1987). A vaccinia/VP16 recombinant clone was selected by DNA dot blot hybridization. Expression of VP16 was verified by Western Blot and radioimmunoprecipitation, and the recombinant clone was subsequently purified. The details of this procedure are as follows.

In order to obtain recombinants of pHS225 with vaccinia WR, confluent monolayers of BSC40 cells in T-25 flasks were infected with WR at a multiplicity of infection (moi) of 0.05; adsorption was performed for two hours at room temperature with rocking. Three pHS225 solutions were prepared with Lipofectin as follows: 50 μl of a DNA solution containing either 1, 10, or 100 μg pHS225 in water were mixed with 30 μg Lipofectin™ plus 20 μl water. The solutions were allowed to incubate at room temperature for 15 minutes. The infected cells were washed twice in serum free medium; 3 ml of serum free medium was added to each flask; then 100 μl of a DNA-Lipofectin™ complex was added dropwise to each flask with swirling. Transfections were incubated at 37° in an atmosphere containing 7% $CO_2$ for 5 hours. Then 3 mls of DME containing 20% fetal calf serum (FCS) was added to each flask (final FCS concentration was 10%), and the transfections were incubated for 48–72 hours. After the incubation, recombinant virus was harvested by scraping the cells into the medium. Virus was released from the cells by freeze-thawing the cells three times.

Recombinant viruses containing VP16 were selected using the technique of Mackett et al. (1987). Briefly, the virus stock generated by each transfection was thawed, sonicated and incubated 30 min. at 37° C. in the presence of 0.1 volume of 0.25% trypsin. Monolayers of TK-143 cells were infected with 10-fold serial dilutions of the trypsinized stock. After adsorption, the cells were overlaid with DME containing 1% low melting point agarose, 5% FCS and 25 μg BUDR (Sigma Chemical Co.). At 48 hours post infection (p.i.), the cells were stained with 1% agarose containing 0.1% neutral red. After 3 to 5 hours, viral plaques were visualized as clearings in the cell lawn. Plaques were picked, and subjected to two more rounds of plaque purification using BUDR.

Verification that the selected recombinants contained the VP16 encoding sequence was accomplished by dot blot hybridization. The dot blot technique was essentially according to the technique of Mackett et al. (1987), except that detection was with a fragment encoding VP16. Briefly, cells infected with putative recombinants were dotted onto nitrocellulose using a dot blot manifold, lysed and denatured. Filters were baked at 80° C. in vacuo for 2 hours, treated before hybridization with a solution containing 60% formamide, 1% sodium dodecyl sulfate (SDS), 1M NaCl, 10% dextran sulfate, and hybridized with $10^6$ cpm/ml of [$^{32}$P] labeled VP16. Hybridizations were carried out overnight at 42° C. in a solution containing 60% formamide, 1% sodium dodecyl sulfate (SDS), 1M NaCl, 10% dextran sulfate, 10 mg/ml salmon sperm DNA, 10 mg/ml poly A$^+$ DNA and 50 mg/ml yeast tRNA. After hybridization, the filters were washed four times with 2×SSC for 5 minutes at room temperature, once with 2×SSC, 0.1% SDS for 30 minutes at 65° C., and once with 0.1×SSC, 0.1% SDS for 30 minutes at 65° C. The results of the hybridization showed that 6 of 12 isolates were positive for the HSV-2 VP16 coding sequence, and that 2 of the 12 isolates were strongly positive. Six isolates prepared as described above were chosen for further analysis of the expression of VP16.

Example 3
Expression of VP16 from Recombinant vv-VP16 Vectors

Expression of VP16 from the vv-VP16 clones described in Example 2 was detected by radioimmunoprecipitation of [$^{35}$S]-labeled infected cell lysates using high-titer positive human sera followed by SDS-polyacrylamide gel electrophoresis of the precipitated products, and subsequent visualization of [$^{35}$S]-labeled-VP16 by autoradiography. More specifically, the samples were electrophoresed on 8%, 1.5 mm thickness polyacrylamide gels (Novex Corp.) for 90 minutes at 40 mA. After electrophoresis the gels were fixed, "enhanced" and dried prior to exposure to film. The apparent molecular weight of the recombinant VP16 (Vmw65) is 65 kD. The identity of VP16 was confirmed by radioimmunoprecipitation of protein from HSV-2 infected Vero cells, using the VP16 specific monoclonal antibody, LP1, for the precipitation. LP1, which is described in McLean et al. (1982), was obtained from A. Minson, Cambridge University. The labeled precipitated product from the vv-VP16 infected cells co-migrated during electrophoresis with the labeled precipitated product from the Vero cells. This co-migration during electrophoresis of the VP16 expressed in Vero cells and from the recombinant vaccinia virus-VP16 (vv-VP16) cells indicate that the vv-VP16 product is full length.

It is of interest that the antibody LP1 does not recognize VP16 expressed in the vv-VP16 cells, whereas it does recognize VP16 expressed in HSV infected Vero cells. It is possible that the change in antibody recognition in the vv-VP16 product results from a lack of phosphorylation of the recombinantly produced polypeptide, or other differences in protein processing, since vaccinia virus replicates in the cytoplasm of the infected cell.

Example 4
Immunogenicity and Protective Effect of Immunization with VP16 or gB2

Figure 7:
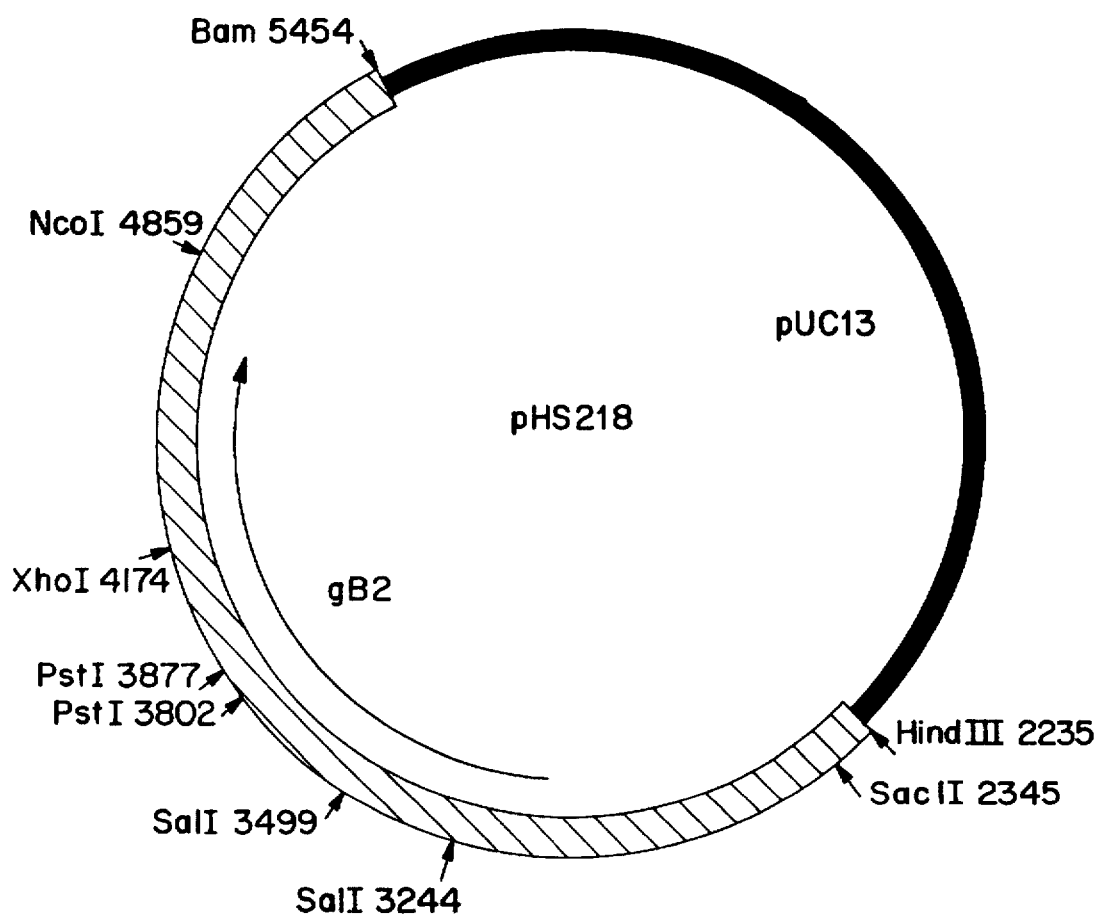
FIG. 7 is a map showing some significant features of the vector pHS218.
Figure 8:
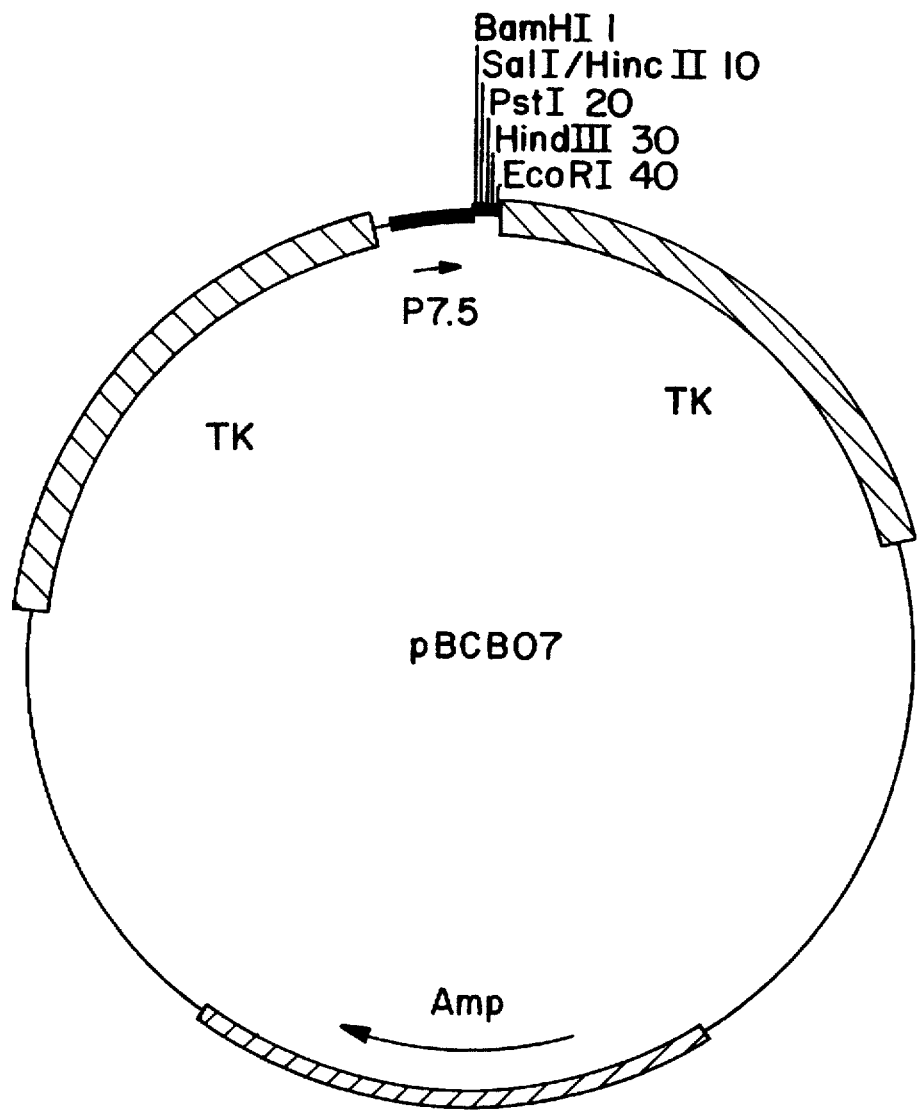
FIG. 8 is a map showing some significant features of the vector pBCB07.
Figure 9:
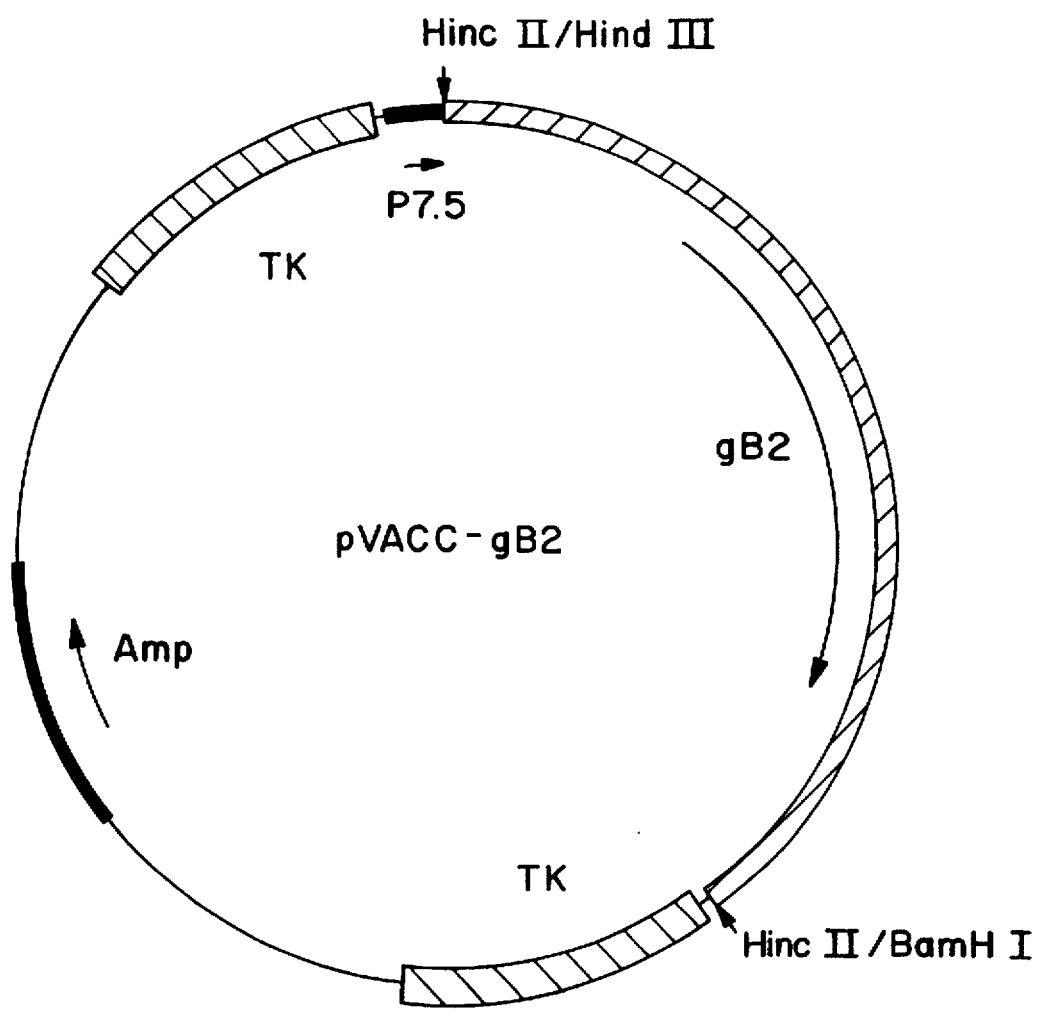
FIG. 9 is a map showing some significant features of the vector pVACC-gB2.

In order to compare the effect of immunization with VP16 to that with gB2, with respect to their immunogenicity and protection against HSV-2 caused disease, vaccinia virus recombinants encoding each polypeptide were used to immunize guinea pigs. The vaccinia recombinant used which contains the gene coding for VP16 was that described in Example 2, i.e., vv-VP16 (also called vv-VP16-TK⁻). The gB recombinant was prepared by subcloning a polynucleotide encoding gB2 into a pUC13 vector. The gB2 encoding polynucleotide, which was a 3.2 Kb HindIII-BamHI fragment, contained nucleotides from position −136 to 3088, as shown in FIG. 4 in WO88/02634; the latter figure is included herein as FIGS. 6A through 6E. Significant features of the resulting vector, pHS218, are shown in FIG. 7. In order to produce a vaccinia virus expression vector encoding gB2, a 3.2 Kb HindIII-BamHI fragment excised from pHS218 was blunt ended, and ligated into the HincII site of pCB07 yielding the vector, pVACC-gB2⁻. Significant features of the vectors pCB07 and pVACC-gB2 are shown in FIG. 8 and FIG. 9, respectively. Similar to the vv-VP16 construct, this places the vaccinia promoter, 7.5, upstream of the gene; the flanking thymidine kinase (TK) sequences provide for recombination into the wild type virus at this locus. The construction of pVACC-gB2 from pHS218 was performed by Dr. Ian Ramshaw, The John Curtin School of Medical Research, The Australian National University, Canberra, Australia. The procedures for the production of the vaccinia expression vector, vv-gB2, from wild-type vaccinia virus were similar to those for the production of vv-VP16, except that recombination was with pVACC-gB2, and selection for positive clones was by hybridization with a radiolabeled fragment encoding gB2.

Female guinea pigs were immunized either intradermally (by scarification of the skin below the right intercostal margin with a bifurcated needle), interperitoneally, or intravenously (into an ear vein using a 30 gauge needle). The protocols for each of the groups in the study are shown in the following Table 1.

TABLE 1

Immunization with vv-gB2 or vv-VP16

| Group | Route of Immunization | Immunizations I & II |
|---|---|---|
| 1 | I.D. | $10^8$ pfu vv-gB2 |
| 2 | I.P. | $10^8$ pfu vv-gB2 |
| 3 | I.V. | $10^8$ pfu vv-gB2 |
| 4 | I.D. | $10^8$ pfu vv-VP16 |
| 5 | I.P. | $10^8$ pfu vv-VP16 |
| 6 | I.V. | $10^8$ pfu vv-VP16 |

The animals were immunized twice with a one-month interval between immunizations. The animals were bled for the determination of HSV-specific and vaccinia-specific neutralizing antibodies at 3 and 6 weeks following the second immunization. Animals in groups 1 through 6 were challenged with $3 \times 10^5$ pfu of HSV-2 strain MS; challenge was on day 64, 6 weeks after the second immunization boost. Challenge was by intravaginal inoculation of HSV-2. The animals were scored for acute disease the first 14 days post-challenge.

Figure 10:
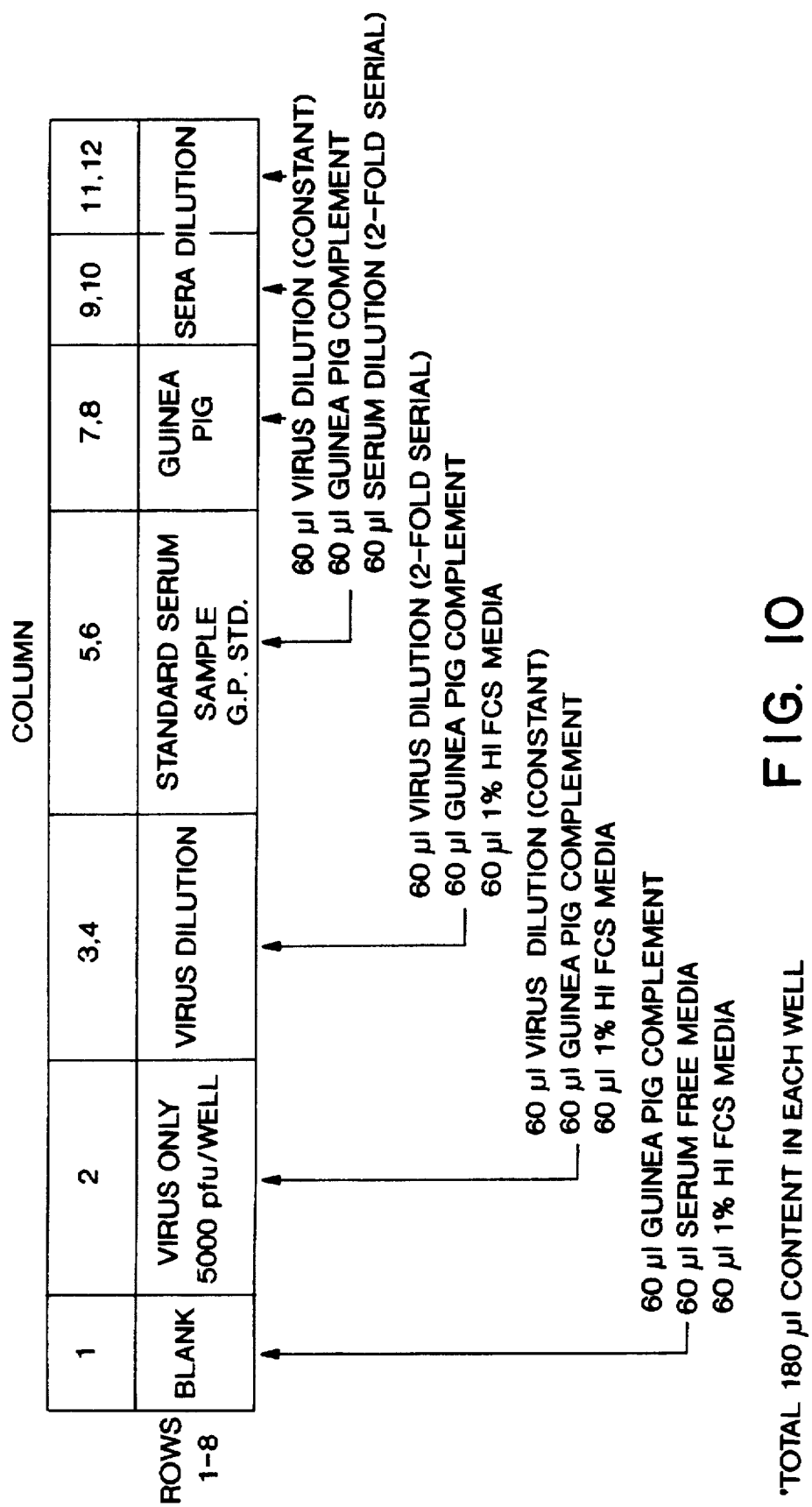
FIG. 10 is a schematic showing the contents of wells in an antibody titer study.

In order to measure the immunogenicity of VP16 and gB2, the titers of neutralizing antibodies resulting from the immunizations, both complement dependent and complement independent, were determined as follows. A suspension of 150 µl of Vero cells ($1.1 \times 10^6$ cells per 15 ml medium containing 10% fetal calf serum (FCS)) were seeded in two 96 well flat bottom plates (Micro Test® III, Becton, Dickinson and Co., Franklin Lakes, N.J.), and incubated overnight in a $CO_2$ incubator at 37° C. On the next day, samples were prepared in a third 96 well plate, the well contents were as shown in FIG. 10. In the figure, the medium was DME-H21 tissue culture medium, heat-inactivated fetal calf serum (HI FCS) was prepared by incubating FCS (Hyclone Corp.) at 56° C. for 30 min., the guinea pig complement was a 1:125 dilution of rehydrated guinea pig complement (Gibco Corp., prepared according to the manufacturer's directions). A fourth plate was also prepared, which was analogous to the third plate, but in which the guinea pig complement was omitted. The plates were incubated for 2 hours. Viral absorption and replication was accomplished by aspirating the culture medium from the cell monolayers in plates 1 and 2. The contents of the corresponding wells in plates 3 and 4 were transferred to plates 1 and 2, respectively, and the plates were maintained in a $CO_2$ incubator at 37° C. for three days. In order to detect cell cytolysis due to viral replication, after the three day incubation, the culture medium was aspirated from the cells, 100 µl of a phosphate buffered saline solution containing 10% formaldehyde solution and 0.09% crystal violet was added to each well. The plates were incubated 15 min at room temperature, the crystal violet solution was removed, and the wells were washed three times with water and the plates were air dried. The viral titers were $3(2^n)$ and $2(2^n)$ for the complement dependent and complement independent samples, respectively; n equals the serum dilution that inhibits cytolysis of the cell monolayer by 50%.

Figure 11:
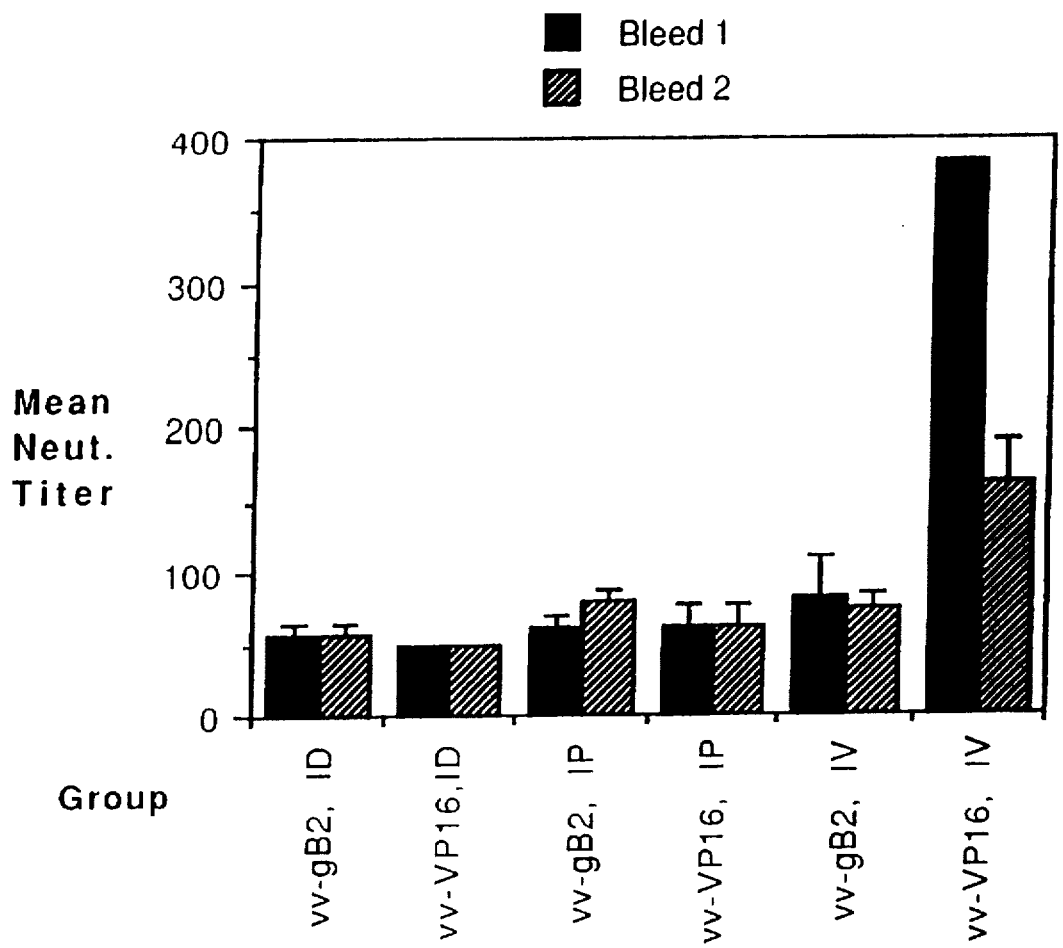
FIG. 11 is a bar graph showing the titer of HSV specific complement dependent neutralizing antibody titers resulting from immunization with vv-gB2 and vv-VP16.

The results on the antibody titrations, expressed as the mean neutralizing titers found in bleeds 1 and 2 for HSV-specific complement dependent neutralizing antibody titers are shown in FIG. 11. As seen in the figure, at 3 weeks (bleed 1), I.V. administration of vv-VP16 increased the complement dependent neutralizing antibodies approximately five-fold higher than did vv-gB2.

The HSV-specific complement independent neutralizing antibody titers for bleed 1 are shown in the following Table 2. As seen from the Table 2, I.V. administration of vv-VP16 yielded titers of antibodies which exceeded HSV-specific titers induced by the vv-gB2 recombinant by >10 fold. Neutralization was determined as 50% reduction in plaque formation. Animals immunized with wild-type non-recombinant vaccinia, WR, do not elicit measurable neutralizing antibodies.

TABLE 2

HSV-Specific Complement-Independent Neutralizing Antibody Titers

| Group | Vaccine | Administration | Titer $2_3$* |
|---|---|---|---|
| 1 | vv-gB2 | I.D. | 32 ± 0 |
| 2 | vv-gB2 | I.P. | 32 ± 0 |
| 3 | vv-gB2 | I.V. | 32 ± 0 |
| 4 | vv-VP16 | I.D. | 32 ± 0 |
| 5 | vv-VP16 | I.P. | 40 ± 8 |
| 6 | vv-VP16 | I.V. | 565 ± 53 |

*Titer $2_3$ signifies the average titer at 3 weeks.

The effect of immunization with vv-VP16 and vv-gB2 on protection as reflected in lesions and the severity of acute disease were also compared. The clinical course of primary genital HSV-2 infection is generally as follows. Lesions first appear on the external genitalia of all animals three to four days after viral inoculation. The lesions begin as discrete vesicles with an erythematous base, and rapidly progress to multiple vesiculo-ulcerative lesions by days 5–8. Hemorrhagic crusts cover the ulcerative lesions by days 8–10. Loss of the crusts with complete healing of the external genital skin occurs by days 13–15. Most animals develop urinary retention between day 5 and day 10; however, this symptom is resolved by days 10–15. Hindlimb paralysis may be evident in 0% to 20% of animals by days 7–10; this symptom is resolved by days 15–20. Infection and external genital lesions occur in 80–100% of the inoculated animals with death rates of 0–50%. The lesion scoring for the studies was according to the following scale:

0.5=redness, swelling;

1.0=1–2 vesicles, or 1 vesicle accompanied by redness and swelling;

1.5=2–4 small vesicles (1–2 mm diameter) or 2 vesicles accompanied by swelling and redness;

2.0=4–6 vesicles 2.5=4–6 large vesicles (greater than 2 mm diameter) with swelling and redness;

3.0=greater than 6 large vesicles;

3.5=greater than 6 large vesicles accompanied by additional smaller vesicles;

4.0=confluent vesicles covering greater than one-half of the perineum;

4.5=extreme vesicles with ulceration.

The results comparing the effect of the immunization with vv-VP16 to vv-gB2 on protection against the disease as indicated by the occurrence and severity of lesions as well as on mortality, are shown in the following Table 3. In the study all animals developed lesions; the lesion score for the unimmunized control group was 3.10.

TABLE 3

Effect of Immunization with vv-gB2 or vv-VP16 on the Clinical Course of Acute Genital HSV-2 Infection

| Group | Vaccine | Route | Lesion Score | Protection | Mortality |
|---|---|---|---|---|---|
| 1 | vv-gB2 | I.D. | 1.89 ± .19 | 39% | 1/4 |
| 2 | vv-gB2 | I.P. | 1.33 ± .15 | 57% | 0 |
| 3 | vv-gB2 | I.V. | 1.29 ± .13 | 58% | 0 |
| 4 | vv-VP16 | I.D. | 2.85 ± .16 | 8% | 1/4 |
| 5 | vv-VP16 | I.P. | 2.33 ± .17 | 25% | 0 |
| 6 | vv-VP16 | I.V. | 1.62 ± .14 | 48% | 0 |

Figure 12:
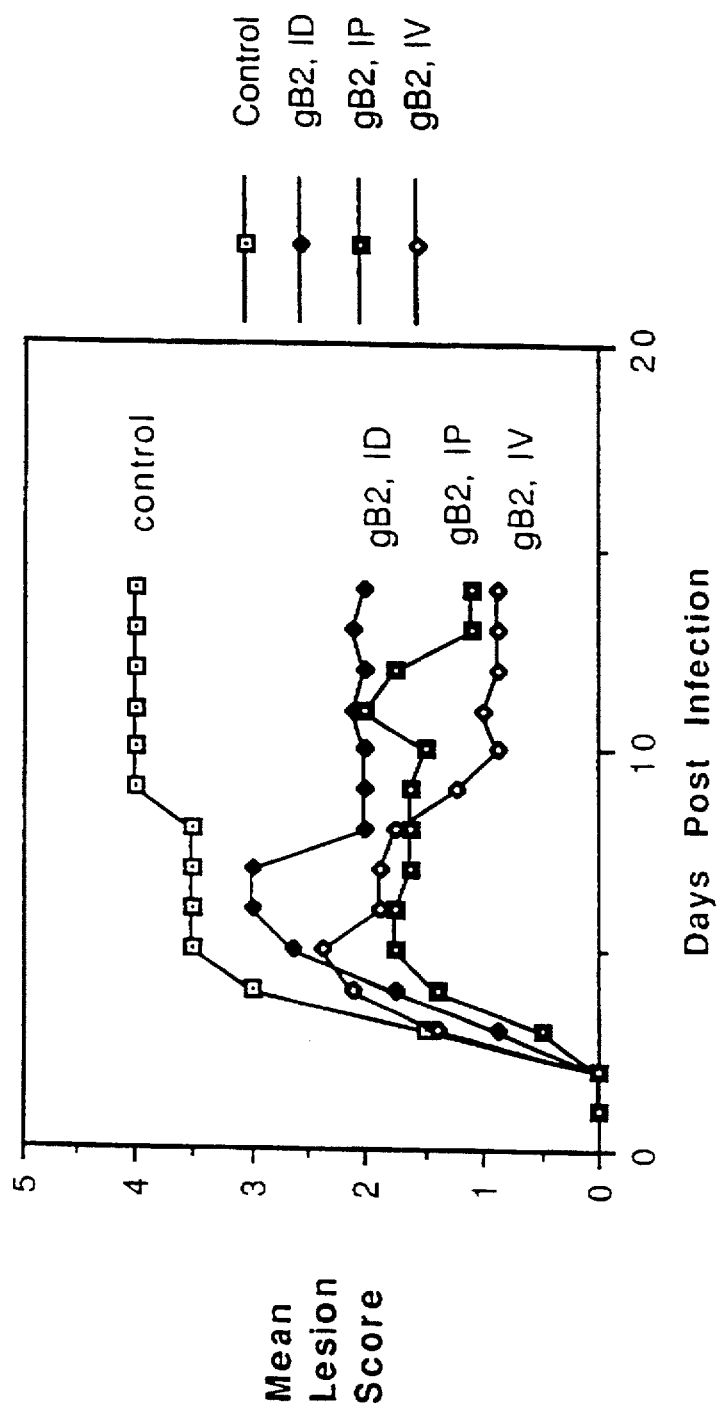
FIG. 12 is a graph showing the time course of protection resulting from immunization with vv-gB2.
Figure 13:
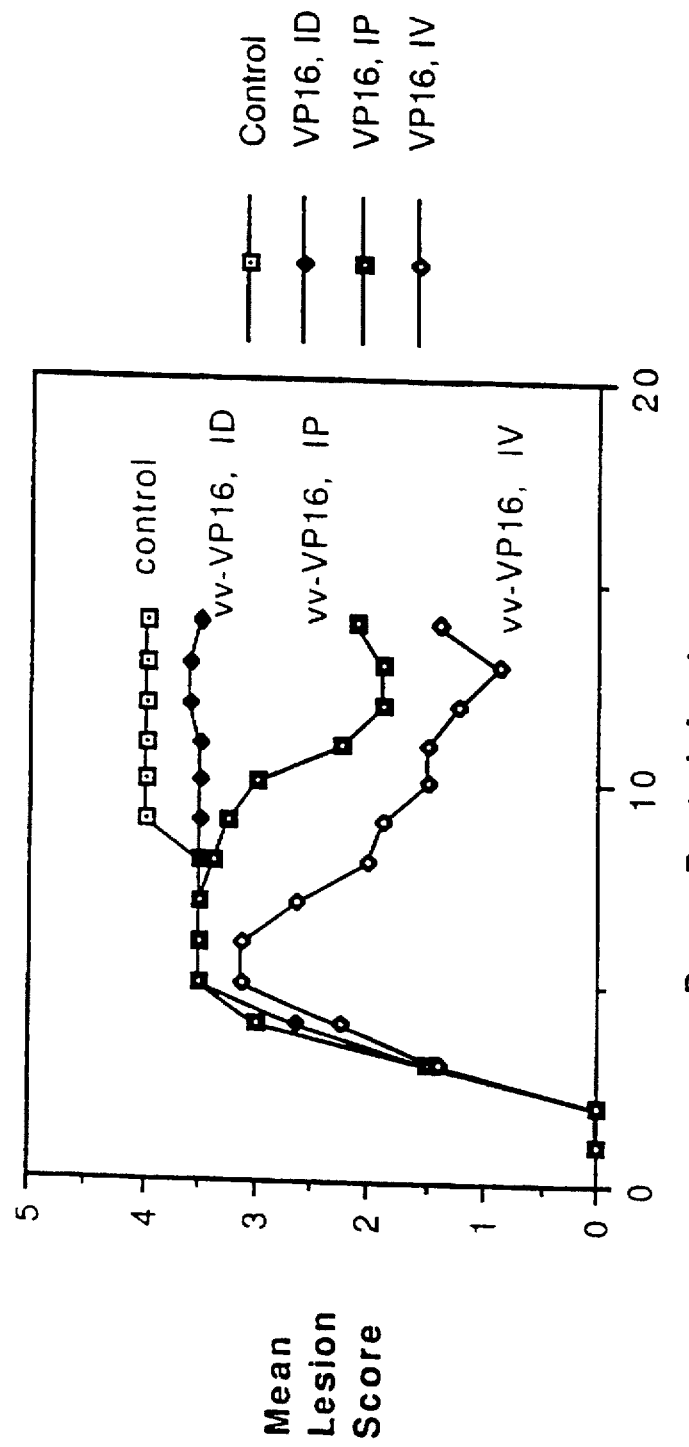
FIG. 13 is a graph showing the time course of protection resulting from immunization with vv-VP16.

The time course of protection with the different routes of immunization with vv-gB2 and vv-VP16 are shown in FIG. 12 and FIG. 13, respectively.

Example 5
Immunogenicity and Protective Effect of Immunization with VP16 and gB2

The immunogenicity and protective effect of vv-VP16 and vv-gB2 against HSV-2 caused disease was examined using a protocol similar to that in Example 4, except that the administration of the vaccines was I.V., and the challenge dose with HSV-2 strain MS was 6×10$^4$ pfu. The vaccines were administered to four groups as follows: group 1, no treatment; group 2, vv-VP16+vv-gB2; group 3, vv-gB2 alone; and group 4, vv-VP16 alone.

The results of the study on the production of complement-dependent neutralizing antibody titers is shown in the following Table 4. In the study, neutralization was determined as 50% reduction in plaque formation. Animals immunized with vaccinia WR do not elicit measurable neutralizing antibodies (<16). These results indicate that, at three weeks post-immunization, treatment with vaccine comprised of both vv-VP16 and vv-gB2 caused higher titers of neutralizing antibodies than did either vv-gB2 or vv-VP16 alone; at six weeks immunization with vv-VP16 and vv-gB2 with respect to the antibody titers.

TABLE 4

Effect of vv-VP16 and vv-gB2 on Complement Dependent Neutralizing Antibody Titers

| Group | Vaccine | Mean Titer (3 weeks) | Mean Titer (6 weeks) |
|---|---|---|---|
| 1 | None | 13 ± 6 | 14 ± 2 |
| 2 | vv-VP16 + vv-gB2 | 590 ± 57 | 500 ± 61 |
| 3 | vv-gB2 | 113 ± 12 | 224 ± 34 |
| 4 | vv-VP16 | 213 ± 39 | 615 ± 61 |

Figure 14:
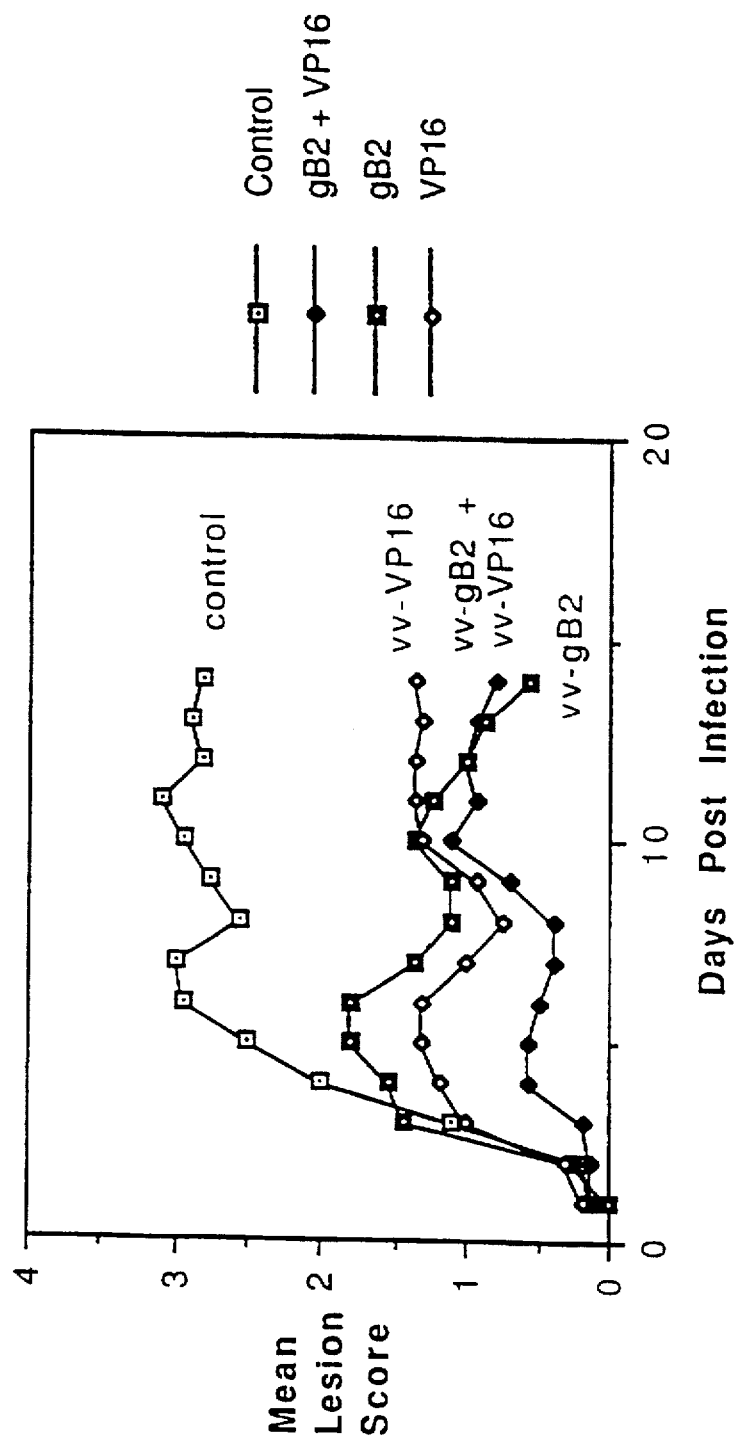
FIG. 14 is a graph showing the time course of protection resulting from immunization with vv-gB2, vv-VP16, and vv-gB2+vv-VP16.

The protective effect of the combined vaccine comprised of vv-VP16 and vv-gB2 relative to the single subunit vaccines was also monitored, using the procedures (with the above modifications) and scoring described in Example 4. In the study, all of the animals exhibited lesions. However, the results, shown in the following Table 5, indicated that the acute disease was ameliorated by the vaccines, and that the protective effect of the combination vaccine was enhanced relative to either vv-gB2 or vv-VP16 alone. The time course of the protective effect is shown in FIG. 14.

TABLE 5

The Effect of vv-VP16 and vv-gB2 on Acute Genital HSV-2 Infection

| Group | Vaccine | Lesion Score | Protection | Mortality |
|---|---|---|---|---|
| 1 | None | 2.27 ± .28 | — | 4/8 (50%) |
| 2 | vv-VP16 + vv-gB2 | 0.59 ± .09 | 74% | 0/8 (0%) |
| 3 | vv-gB2 | 1.12 ± .14 | 50.7% | 0/8 (0%) |
| 4 | vv-VP16 | 1.05 ± .11 | 53.8% | 0/8 (0%) |

The following listed materials are on deposit under the terms of the Budapest Treaty with the American Type Culture Collection (ATCC), 12301 Parklawn Dr., Rockville, Md. 20852, and have been assigned the following Accession Numbers

| Material | Deposit Date | ATCC No. |
|---|---|---|
| pHS226 in *E. coli* DH5α | 15 July 1990 | 68372 |

Upon allowance and issuance of this application as a United States Patent, all restriction on availability of these deposits will be irrevocably removed; and access to the designated deposits will be available during pendency of the above-named application to one determined by the Commissioner to be entitled thereto under 37 CFR 1.14 and 35 USC 1.22. Moreover, the designated deposits will be maintained for a period of thirty (30) years from the date of deposit, or for five (5) years after the last request for the deposit; or for the enforceable life of the U.S. patent, whichever is longer. The deposited materials mentioned herein are intended for convenience only, and are not required to practice the present invention in view of the descriptions herein, and in addition these materials are incorporated herein by reference.

Industrial Applicability

The compositions described herein, which contain an immunogenic polypeptide comprised of an epitope of HSV VP16, are useful for the alleviation of symptoms resulting from herpes simplex virus infections. The recombinant vectors, expression systems, and host cells transformed by these vectors are useful for the preparation of the immunogenic polypeptides, which in turn are useful in the preparation of the above described vaccines.

What is claimed is:

1. A composition for treatment or prevention of herpes simplex virus (HSV) infection in an individual, said composition comprised of an adjuvant, an isolated immunogenic polypeptide of herpes simplex virus type 2 (HSV-2) VP16 capable of eliciting a cellular immune response, said polypeptide comprising at least about the first 400 amino acids of HSV-2 VP16, and wherein the polypeptide is present in an effective amount in a pharmaceutically acceptable excipient.

2. The composition of claim 1, wherein the polypeptide is selected from the group consisting of isolated HSV-2 VP16 and a truncated HSV-2 VP16 comprising at least about the first 400 amino acids of HSV-2 VP16 but less than all the amino acids of full-length HSV-2 VP16.

3. The composition of claim 1 further comprised of an immunogenic epitope of a first isolated HSV glycoprotein selected from the group consisting of gB and gD.

4. The composition of claim 3, wherein the first HSV glycoprotein is gB.

5. The composition of claims 3, wherein the first HSV glycoprotein is gD.

6. The composition of claim 3, further comprised of an immunogenic epitope of a second isolated HSV glycoprotein selected from the group consisting of gB and gD, with the proviso that when the first isolated HSV glycoprotein is a gB polypeptide, the second isolated HSV glycoprotein is a gD polypeptide, and when the first isolated HSV glycoprotein is a gD polypeptide, the second isolated HSV glycoprotein is a gB polypeptide.

7. The composition of claim 3, wherein the first isolated glycoprotein is selected from the group consisting of an HSV gB, an HSV gD, a truncated HSV gB and a truncated HSV gD.

8. The composition of claim 6, wherein the second isolated glycoprotein is selected from the group consisting of an HSV gB, an HSV gD, a truncated HSV gB and a truncated HSV gD.

9. A composition comprised of recombinant vaccinia virus, wherein the virus is comprised of a sequence encoding an immunogenic polypeptide of herpes simplex virus type 2 (HSV-2) VP16 capable of eliciting a cellular immune response, said polypeptide comprising at least about the first 400 amino acids of HSV-2 VP16, wherein the polynucleotide encoding the immunogenic polypeptide is operably linked to a control sequence.

10. The composition of claim 9, further comprised of recombinant vaccinia virus which is comprised of a polynucleotide encoding an HSV glycoprotein selected from the group consisting of gB and gD operably linked to a control sequence.

11. A composition prepared according to the method comprising:

(a) providing an isolated immunogenic polypeptide of herpes simplex virus type 2 (HSV-2) VP16 capable of eliciting a cellular immune response, said polypeptide comprising at least about the first 400 amino acids of HSV-2 VP16;

(b) providing an adjuvant; and (c) formulating the polypeptide and adjuvant in a pharmaceutically acceptable excipient.

12. A composition according to claim 11, wherein the method of producing the composition further comprises providing an immunogenic epitope of a first isolated HSV glycoprotein selected from the group consisting of gB and gD.

13. A composition according to claim 12, wherein the method of producing the composition further comprises providing an immunogenic epitope of a second isolated HSV glycoprotein selected from the group consisting of gB and gD, with the proviso that when the first isolated glycoprotein is a gB polypeptide, the second isolated glycoprotein is a gD polypeptide, and when the first isolated glycoprotein is a gD polypeptide, the second isolated glycoprotein is a gB polypeptide.

14. A method of treating or preventing HSV infection in an individual comprising administering to the individual the composition of claim 1.

15. A method of treating and/or preventing HSV infection in an individual comprising administering to the individual the composition of claim 3.

16. A method of treating or preventing HSV infection in an individual comprising administering to the individual the composition of claim 8.

* * * * *